US006800649B1

(12) United States Patent
Uckun

(10) Patent No.: US 6,800,649 B1
(45) Date of Patent: Oct. 5, 2004

(54) METHOD FOR INHIBITING C-JUN EXPRESSION USING JAK-3 INHIBITORS

(75) Inventor: Fatih M. Uckun, White Bear Lake, MN (US)

(73) Assignee: Parker Hughes Institute, St. Paul, MN (US)

( * ) Notice: Subject to any disclaimer, the term of this patent is extended or adjusted under 35 U.S.C. 154(b) by 0 days.

(21) Appl. No.: 09/345,815

(22) Filed: Jun. 30, 1999

Related U.S. Application Data

(60) Provisional application No. 60/091,150, filed on Jun. 30, 1998.

(51) Int. Cl.$^7$ .............................................. A01N 43/40
(52) U.S. Cl. ........................ 514/345; 514/345; 514/293; 514/292; 514/187; 514/418; 514/266.4; 514/346; 514/445; 514/369; 514/414; 514/184; 514/342; 514/363; 514/228.2; 514/234.5; 514/253; 514/235.2; 514/254.09; 424/134.1; 424/145.1
(58) Field of Search ................................ 514/293, 345, 514/292, 187, 418, 266.4, 346, 445, 369, 414, 184, 342, 363, 228.2, 234.5, 253, 235.2, 254.09; 424/134.1, 145.1; 544/293, 292

(56) References Cited

U.S. PATENT DOCUMENTS

| | | | |
|---|---|---|---|
| 4,322,420 A | 3/1982 | Kobayashi et al. | ......... 424/251 |
| 4,343,940 A | 8/1982 | Kreighbaum et al. | ....... 544/283 |
| 4,464,375 A | 8/1984 | Kobayashi et al. | ......... 424/251 |
| 4,559,157 A | 12/1985 | Smith et al. | .................. 252/90 |
| 4,608,392 A | 8/1986 | Jacquet et al. | .............. 514/844 |
| 4,820,508 A | 4/1989 | Wortzman | .................... 424/59 |
| 4,938,949 A | 7/1990 | Borch et al. | .................. 424/10 |
| 4,992,478 A | 2/1991 | Geria | .......................... 514/782 |
| 5,710,158 A | * 1/1998 | Myers et al. | ............... 514/259 |
| 5,792,771 A | 8/1998 | App et al. | ................... 514/259 |

FOREIGN PATENT DOCUMENTS

| | | |
|---|---|---|
| WO | 95/03701 | 2/1995 |
| WO | 95/15758 | 6/1995 |
| WO | 96/09294 | 3/1996 |
| WO | 96/40648 | 12/1996 |
| WO | 97/03358 | 1/1997 |

OTHER PUBLICATIONS

Myers, et al., "The Preparation and SAR of 4–(Anilino), 4–(Phenoxy), and 4–(Thiophenoxy)–Quinazolines: Inhibitors of p56lck and EGF–R Tyrosine Kinase Activity", 1997, Bioorganic and Medicinal Chemistry Letters, vol. 7, No. 4, pp. 417–420.*

Karin, et al., "AP–1 Function and Regulation", 1997, Cell Biology, 9:240–246.*

Riedy et al., "Genomic Sequence, Organization, and Chromosomal Localization of Human JAK–3", 1996, Genomics 37: 57–61.*

Chae, et al "Role of Tyrosine Phosphorylation in Radiation–induced Activation of c–jun Protooncogene in Human Lymphohematopoietic Precursor Cells", 1993, Cancer Research 53:447–451.*

Bridges, A.J., et al., "Tyrosine kinase inhibitors. 8. An unusally steep structure–activity relationship for analogues of 4–(3–bromoanilino)–6,7–dimethoxyquinazoline (PD 153035), a potent inhibitor of the epidermal growth factor receptor", *J. Med. Chem.*, *39*, pp. 267–276, (1996).

Budesinsky, Z., et al., "A new synthesis of the quinazoline nucleus", *Collection Czechoslov Chem. Commun.*, *37* (*8*), pp. 2779–2785, (1972).

Fetter, J., et al., "Electron deficient heteroraromatic ammonioamidates–XVI$^a$—The synthesis and photochemistry of ethyl N–(2–methyl–4–metehylene–6,7–methylenedioxy–3, 4–dihydro–3–quinzolinyl)–N–phen ylcarbamate", *Tetrahedron*, *34* (*16*), pp. 2557–2563, (1978).

Goodman, P.A., et al., "Role of tyrosine kinases in induction of the c–jun proto–oncogene in irradiated B–lineage lymphoid cells", *The Journal of Biological Chemistry, 273* (*28*), pp. 17742–17748, (1998).

Higashino, T., et al., "Reactions of the anion of quinazoline reissert compound (3–benzoyl–3, 4–dihydro–4–quinazolinecarbonitrile) with electrophiles", *Chem. Pharm. Bull.*, *33* (*3*), pp. 950–961, (1985).

Ife, R.J., et al., "Reversible inhibitors of the gastric ($H^+/K^+$)–ATPase. 5. Substituted 2,4–diaminoquinazolines and thienopyrimidines", *J. Med. Chem.*, *38*, pp. 2763–2773, (1995).

Kubo, K., et al., "A Novel series of 4–phenoxyquinolines: potent and highly selective inhibitors of pdgf receptor autophosphorylation", *Bioorganic & Medicinal Chemistry Letters, 7* (*23*), pp. 2935–2940, (1997).

Malaviya, R., et al., "Genetic and Biochemical evidence for a critical role of Janus Kinase (JAK)–3 in mast cell–mediated type I hypersensitivity reactions", *Biochemistry and Biophysical Research Communications, 257* (*3*), pp. 807–813, (1993).

(List continued on next page.)

*Primary Examiner*—Christopher S. F. Low
*Assistant Examiner*—Hope A. Robinson
(74) *Attorney, Agent, or Firm*—Merchant & Gould P.C.

(57) ABSTRACT

The invention provides a method for inhibiting c-jun activation in mammalian or avian cells comprising contacting the cells with a substance that inhibits the activity of Janus family kinase 3 (JAK-3). The invention also provides a therapeutic method for preventing or treating a pathological condition in a mammal wherein c-jun activation is implicated and inhibition of its activation is desired comprising administering to a mammal in need of such therapy, an effective amount of a substance that inhibits the activity of JAK-3. Novel compounds that are JAK-3 inhibitors, as well as pharmaceutical compositions comprising the compounds are also provided.

8 Claims, 11 Drawing Sheets

OTHER PUBLICATIONS

Miyashita, A., et al., "An approach to the synthesis of a pavaverine analogue containing a quinazoline ring system", *Heterocycles*, 40 (2), pp. 653–660, (Mar. 1995).

Myers, M.R., et al., "The preparation and sar of 4–(anilino), 4–(phenoxy), and 4–(thiophenoxy)–quinazolines: inhibitors of p56[lck] adn EGF–R tyrosine kinase activity", *Bioorganic & Medicinal Chemistry Letters*, 7 (4), pp. 417–420, (1997).

Narla, R.K., et al., "4–(3'–Bromo–4'hydroxylphenyl)–amino–6,7–dimethoxyquinazoline: A Novel quinazoline derivative with potent cytotoxic activity against human glioblastoma cells", *Clinical Cancer Research*, 4 (6), pp. 1405–1414, (Jun. 1998).

Aoki, Y., et al., "Bruton Tyrosine Kinase is Tryosine Phosphorylated and Activated in pre–B Lymphocytes and receptor–ligated B cells", *Proceedings of the National Academy of Sciences*, 91 (22), pp. 10606–10609, (Oct. 25, 1994).

Bohmann, D., et al., "Human Proto–Oncogene c–jun Encodes a DNA Binding Protein with Structural and Functional Properties of Transcription Factor AP–1", *Science*, 238, pp. 1386–1392, (Dec. 4, 1987).

Chae, H.P., et al., "Role of Tyrosine Phosphorylation in Radiation–Induced Activation of c–jun Protooncogene in Human Lymphohematopoietic Precursor Cells[1]", *Cancer Research*, 53 (3), pp. 447–451, (Feb. 1, 1993).

Chen, Y., et al., "The Role of c–Jun N–terminal Kinase (JNK) in Apoptosis Induced by Ultraviolet C and γ Radiation", *The Journal of Biological Chemistry*, 271 (50), pp. 31929–31936, (Dec. 13, 1996).

Chomczynski, P., et al., "Single–Step Method of RNA Isolation by Acid Guanidinium Thiocyanate–Phenol–Chloroform Extraction", *Analytical Biochemistry*, 162(1), pp. 156–159, (Apr. 1987).

Colotta, F., et al., "Expression and Involvement of c–fos and c–jun Protooncogenes in Programmed Cell Death Induced by Growth Factor Deprivation in Lymphoic Cell Lines", *The Journal of Biological Chemistry*, 267 (26), pp. 18278–18283, (Sep. 15, 1992).

Danial, N.N., et al., "Jak–STAT Signaling Induced by the v–abl Oncogene", *Science*, 269, pp. 1875–1877, (Sep. 29, 1995).

Derijard, B., et al., "JNK1: A Protein Kinase Stimulated by UV Light and Ha–Ras That Binds and Phosphorylates the c–Jun Activation Domain", *Cell*, 76 (6), pp. 1025–1037, (Mar. 25, 1994).

Dibirdik, I., et al., "Stimulation of Src Family Orotein–tyrosine Kinases as a Proximal and Mandatory Step for SYK Kinase–dependent Phospholipase Cγ2 Activation in Lymphoma B Cells Exposed to Low Energy Electromagnetic Fields", *The Journal of Biological Chemistry*, 273(7), pp. 4035–4039, (Feb. 13, 1998).

Dosch, J., et al., "Induction of c–fos, c–jun, junB and junD mRNA and AP–1 by alkylating mutagens in cells deficient and proficient for the DNA repair protein O[6]–methylguanine–DNA methyltransferase (MGMT) and its relationship to cell death, mutation induction and chromosoma", *Onogene*, 13 (9), pp. 1927–1935, (Nov. 1996).

Gurniak, C.B., et al., "Murine JAK3 is Preferentially Expressed in Hematopoietic Tissues and Lymphocyte Precursor Cells", *Blood*, 87 (8), pp. 3151–3160, (Apr. 15, 1996).

Ham, J., et al., "Ac–Jun Dominant Negative Mutant Protects Sympathetic Neurons against Programmed Cell Death", *Neuron*, 14 (5), pp. 927–939, (May 1995).

Hanissian, S.H., et al., "Jak3 Is Associated with CD40 and Is Critical for CD40 Introduction of Gene Expression in B Cells", *Immunity*, 6 (4), pp. 379–387, (Apr. 1997).

Hibbs, M.L., et al., "Multiple Defects in the Immune System of Lyn–Deficient Mice, Culminating in Autoimmune Disease", *Cell*, 83 (2), pp. 301–311, (Oct. 20, 1995).

Hibi, M., et al., "Identification of an oncoprotein–and UV–responsive protein kinase that binds and potentiates the c–Jun activation domain", *Genes & Development*, 7 (11), pp. 2135–2148, (Nov. 1993).

Hoffman, S.M., et al., "JAK3 Maps to Human Chromosome 19p12 within a Cluster of Proto–oncogenes and Transcription Factors", *Genomics*, 43, pp. 109–111, (1997).

Ihle, J.N., "Janus kinases in cytokine signalling", *Philosophical Transactions: Biological Sciences*, 351 (1336), pp. 159–166, (Feb. 29, 1996).

Jugloff, L.S., et al., "Cross–linking of the IgM Receptor Induces Rapid Translocation of IgM–Associated Ig α, Lyn, and Syk Tyrosine Kinases to the Membrane Skeleton[1]", *The Journal of Immunology*, 159 (3), pp. 1096–1106, (Aug. 1, 1997).

Karin, M., et al., "AF–1 Function and Regulation", *Current Opinion in Cell Biology*, 9 (2), pp. 240–246, (Apr. 1997).

Kharbanda, S.M., et al., "Transcriptional Regulation of c–jun Gene Expression by Arabinofuranosylcytosine in Human Myeloid Leukemia Cells", *The Journal of Clinical Investigation*, 86(5), pp. 1517–1523, (Nov. 1990).

Kumar, A., et al., "Structural Organization and Chromosomal Mapping of JAK3 Locus", *Onogene*, 13 (9), pp. 2009–2014, (Nov. 7, 1996).

Kurosaki, T., "Molecular Mechanisms in B Cell Antigen Receptor Signaling", *Current Opinion in Immunology*, 9 (3), pp. 309–318, (Jun. 1997).

Kurosaki, T., et al., "Role of the Syk Autophosphorylation Site and SH2 Domains in B Cell Antigen Receptor Signaling", *The Journal of Experimental Medicine*, 182 (6), pp. 1815–1823, (Dec. 1, 1995).

Law, D.A., et al., "B–Cell Antigen Receptor Motifs have Redundant Signalling Capabilities and Bind the Tyrosine Kinases PTK72, Lyn and Fyn", *Current Biology*, 3 (10), pp. 645–657, (Oct. 1, 1993).

Leonard, W.J., "STATs and Cytokine Specificity", *Nature Medicine*, 2 (9), pp. 968–969, (Sep. 1996).

Levy, D.E., "The House that JAK/STAT Built", *Cytokine & Growth Factor Reviews*, 8 (1), pp. 81–90, (Mar. 1997).

Mitchell, P.D., et al., "Transcriptional Regulation in Mammalian Cells by Sequence–Specific DNA Binding Proteins", *Science*, 245, pp. 371–378, (Jul. 21, 1989).

Musti, A.M., et al., "Reduced Ubiquitin–Dependent Degradation of c–jun After Phosphorylation by MAP Kinases", *Science*, 275, pp. 400–402, (Jan. 17, 1997).

Myers, D.E., et al., "Membrane–associated CD19–LYN complex is an endogenous p53–independent and Bcl–2–independent regulator of apoptosis in human B–lineage lymphoma cells", *Proceedings of the National Academy of Sciences*, 92 (21), pp. 9575–9579, (Oct. 10, 1995).

Neuberg, M., et al., "A Fos protein containing the Jun leucine zipper forms a homodimer which binds to the AP1 binding site", *Nature* 341 (6239), pp. 243–245, (Sep. 21, 1989).

Nomoto, Y., et al., "Studies on Cardiotonic Agents. I. Synthesis of Some Quinazoline Derivatives", *Chemical & Pharmaceutical Bulletin*, 38 (6), pp. 1591–1595, (Jun. 1990).

Nosaka, T., et al., "Defective Lymphoid Development in Mice Lacking Jak3", *Science, 270*, pp. 800–802, (Nov. 3, 1995).

QIn, S., et al., "Syk–dependent and –independent Signaling Cascades in B Cells Elicited by Osmotic and Oxidative Stress", *The Journal of Biological Chemistry, 272 (4)*, pp. 2098–2103, (Jan. 24, 1997).

Riedy, M.C., et al., "Genomic Sequence, Organization, and Chromosomal Localization of Human JAK3", *Genomics, 37 (1)*, pp. 57–61, (Oct. 1, 1996).

Rolling, C., et al., "IL4 abd IL13 Receptors share the γc chain and activate STAT6, STAT3 and STAT5 proteins in normal human B cells", *FEBS Letters, 393 (1)*, pp. 53–56, (Sep. 9, 1996).

Rolling, C., et al., "JAK3 associates with the human Interleukin 4 receptor and is tyrosine phosphorylated following receptor triggering", *Onogene, 10 (9)*, pp. 1757–1761, (May 4, 1995).

Rosette, C., et al., "Ultraviolet Light and Osmotic Stress: Activation of the JNK Cascade Through Multiple Growth Factor and Cytokine Receptors", *Science, 274*, pp. 1194–1197, (Nov. 15, 1996).

Rubin, E., et al., "Activation of the c–jun Protooncogene in Human Myeloid Leukemia Cells Treated With Etoposide", *Molecular Pharmacology, 39 (6)*, pp. 697–701, (Jun. 1991).

Ryder, K., et al., "A Gene Activated by Growth Factors is Related to the Oncogene v–jun", *Proceedings of the National Academy of Sciences, 85 (5)*, pp. 1487–1491, (Mar. 1988).

Safford, M.G., et al., "JAK3: Expression and Mapping to Chromosome 19p12–13.1", *Experimental Hematology, 25 (5)*, pp. 374–386, (May 1997).

Saouaf, S.J., et al., "Temporal Differences in the Activation of Three Classes of Non–transmembrane Protein Tyrosine Kinases Following B–cell Antigen Receptor Surface Engagement", *Proceedings of the National Academy of Sciences, 91 (20)*, pp. 9524–9528, (Sep. 27, 1994).

Schutte, J., et al., "jun–B Inhibits and c–fos Stimulates the Transforming and Trans–Activating Activities of c–jun", *Cell, 59 (6)*, pp. 987–997, (Dec. 22, 1989).

Sharfee, N., et al., "Jak3 Activation in Human Lymphocyte Precursor Cells", *Clinical and Experimental Immunology, 108 (3)*, pp. 552–556, (Jun. 1997).

Takata, M., et al., "Requirement of Phospholipase C–γ2 Activation in Surface Immunoglobulin M–induced B Cell Apoptosis", *The Journal of Experimental Medicine, 182 (4)*, pp. 907–914, (Oct. 1, 1995).

Thomis, D.C., et al., "Defects in B Lymphocyte Maturation and T Lymphocyte Activation in Mice Lacking Jak3", *Science, 270*, pp. 794–797, (Nov. 3, 1995).

Tortolani, P.J., et al., "Regulation of JAK3 Expression and Activation in Human B Cells and B Cell Malignancies", *The Journal of Immunology, 155 (11)*, pp. 5220–5226, (Dec. 1, 1995).

Tuel–Ahlgren, L., et al., "Role of Tyrosine Phosphorylation in Radiation–Induced Cell Cycle–Arrest of Leukemia B–Cell Precursors at the G2–M Transition Checkpoint", *Leukemia and Lymphoma, 20 (5/6)*, pp. 417–426, (1996).

Uckun, F.M., et al., "Biotherapy of B–Cell Precursor Leukemia by Targeting Genistein to CD 19–Associated Tyrosine Kinases", *Science, 267*, pp. 886–891, (Feb. 10, 1995).

Uckun, F.M., et al., "BTK as a Mediator of Radiation–Induced Apoptosis in DT–40 Lymphoma B Cells", *Science, 273*, pp. 1096–1100, (Aug. 23, 1996).

Uckun, F.M., et al., "Intrinsic Radiation Resistance of Primary Clonogenic Blasts from Children with Newly Diagnosed B–Cell Precursor Acute Lymphoblastic Leukemia", *The Journal of Clinical Investigation, 91 (3)*, pp. 1044–1051, (Mar. 1993).

Verheij, M., et al., "Requirement for Ceramide–Initiated SAPK/JNK Signalling in Stress–Induced Apoptosis", *Nature, 380 (6569)*, pp. 75–79, (Mar. 7, 1996).

\* cited by examiner

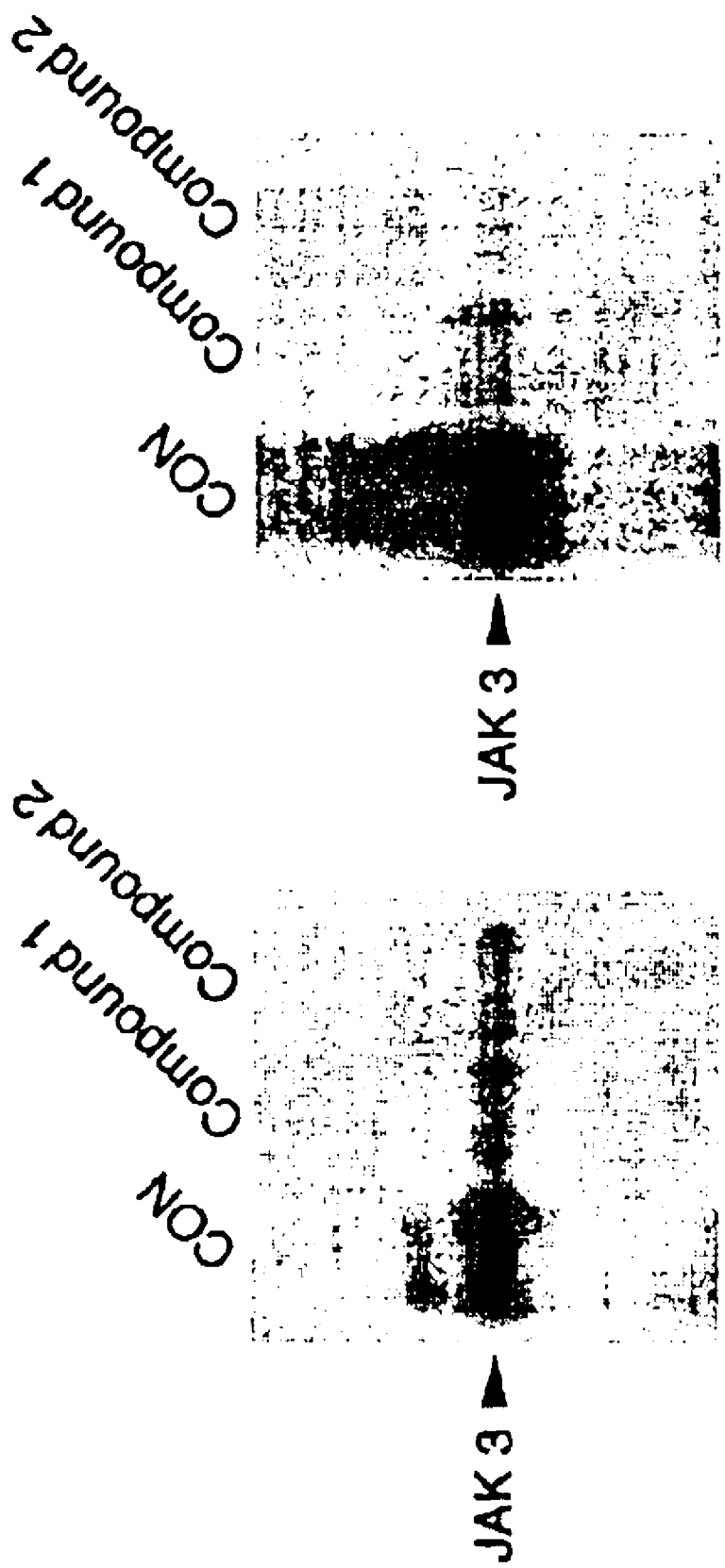

METHOD FOR INHIBITING C-JUN EXPRESSION USING JAK-3 INHIBITORS

PRIORITY OF INVENTION

This application claims priority under 35 U.S.C. §119(e) from U.S. Provisional Application No. 60/091,150, filed Jun. 30, 1998.

BACKGROUND OF THE INVENTION

The protooncogene c-jun is the cellular counterpart of the v-jun. oncogene of avian sarcoma virus 17. C-jun expression is activated in response to a diverse set of DNA-damaging agents including ara-C, UV radiation, topoisomerase II inhibitors, alkylating agents, and ionizing radiation. As an immediate early response gene that is rapidly induced by pleiotropic signals, c-jun may have important regulatory functions for cell cycle progression, proliferation, and survival. See Ryder, K., Lau, L. F., and Nathans, D. "A gene activated by i:3 growth factors is related to the oncogene v-jun," *Proc Natl Acad Sci USA*. 85: 1487–1491, 1988; Schutte, J., Viallet, J., Nau, M., Segal, S., Fedorko, J., and Minna, J. "jun-B inhibits and c-fos stimulates the transforming and trans-activating activities of c-jun, *Cell*. 59: 987–997, 1989; Neuberg, M., Adamkiewicz, J., Hunter, J. B., and Mueller, R. "A fos protein containing the Jun leucine zipper forms a homodimer which binds to the AP-1 binding site," *Nature*. 341: 589–590, 1989; Mitchell, P. J. and Tjian, R. "Transcriptional regulation in mammalian cells by sequence-specific DNA binding proteins," *Science*. 245: 371–378, 1989; Bohmann, D., Bos, T. J., Admon, T., Nishimura, R., Vogt, P. K., and Tijian, R. "Human protooncogene c-jun encodes a DNA binding protein with structural and functional properties of transcription factor AP-1," *Science*. 238: 1386–1392, 1988; Kharbanda, S. M., Sherman, M. L., and Kufe, D. W. "Transcriptional regulation of c-jun gene expression by arabinofuranosylcytosine in human myeloid leukemia cells," *J Clin Invest*. 86: 1517–1523, 1990; Rosette, C. and Karin, M. "Ultraviolet light and osmotic stress: activation of the JNK cascade through multiple growth factor and cytokine receptors," i *Science*. 274: 1194–7, 1996; Rubin, E., Kharbanda, S., Gunji, H., and Kufe, D. "Activation of the c-jun protooncogene in human myleloid leukemia cells treated with etoposide," *Molecular Pharmacology*. 39: 697–701, 1991; Dosch, J. and Kaina, B. "Induction of c-fos, c-jun, junB and junD mRNA and AP-1 by alkylating mutagens in cells deficient and proficient for the DNA repair protein O6-methylguanine-DNA methyltransferase (MGMT) and its relationship to cell death, mutation induction and chromosomal instability," *Oncogene*. 13: 1927–35, 1996; Chae, H. P., Jarvis, L. J., and Uckun, F. M. "Role of tyrosine phosphorylation in radiation-induced activation of c-jun protooncogene in human lymphohematopoietic precursor cells," *Cancer Res*. 53: 447–51, 1993; and Karin, M., Liu, Z.-G., and Zandi, E. "AP-1 function and regulation," *Current Opinion in Cell Biology*. 9: 240–246, 1997.

C-jun encodes the nuclear DNA-binding protein, JUN, that contains a leucine-zipper region involved in homo- and heterodimerization. JUN protein dimerizes with another JUN protein or the product of c-fos gene and forms the activating protein-1 (AP-1) transcription factor. JUN-JUN homodimers and JUN-FOS heterodimers preferentially bind to a specific heptameric consensus sequence found in the promoter region of multiple growth regulatory genes. Alterations of c-jun protooncogene expression can therefore modulate the transcription of several growth-regulators affecting cell proliferation and differentiation. See Ryder, K., Lau, L. F., and Nathans, D. "A gene activated by growth factors is related to the oncogene v-jun," *Proc Natl Acad Sci USA*. 85: 1487–1491, 1988; Neuberg, M., Adamkicwicz, J. Hunter, J. B., and Mueller, R. "A fos protein containing the Jun leucine zipper forms a homodimer which binds to the AP-1 binding site," *Nature*. 341: 589–590, 1989; Karin, M., Liu, Z.-G., and Zandi, E. "AP-1 function and regulation," *Current Opinion in Cell Biology*. 9: 240–246, 1997; Angel, P., Allegretto, E. A., Okino, S. T., Hattori, K., Boyle, W. J., Hunter, T., and Karin, M. "Oncogene jun encodes a sequence-specific trans-activator similar to AP-1," *Nature*. 332: 166–170, 1988; and Musti, A. M., Treier, M., and Bohmann, D. "Reduced ubiquitin-dependent degradation of c-Jun after phosphorylation by MAP kinases," *Science*. 275: 400–402, 1997.

C-jun plays a pivotal role in Ras-induced transformation and has also been implicated as a regulator of apoptosis when de novo protein synthesis is required. C-jun induction is required for ceramide-induced apoptosis and stress-induced apoptosis after UV exposure or other forms of DNA damage. This induction is thought to be triggered by activation of JUN-N-terminal kinases (JNKs) (also known as stress-activated protein kinases) which leads to enhanced c-jun transcription by phosphorylation of JUN at sites that increases its ability to activate transcription. Ectopic expression of a dominant-negative c-jun mutant lacking the N terminus or a dominant-negative JNK kinase abolishes stress-induced apoptosis. See Karin, M., Liu, Z.-G., and Zandi, E. "AP-1 function and regulation," *Current Opinion in Cell Biology*. 9: 240–246, 1997; Collotta, F., Polentarutti, N., and Mantovani, A. "Expression and involvement of c-fos and c-jun protooncogenes in programmed cell death induced by growth factor deprivation in lymphoid cell lines," *J. Biol. Chem*. 267: 18278–18283, 1992; Ham, J., Babij, C., Whitfield, J., Pfarr, C. M., Lallemand, D., Yaniv, M., and Rubin, L. L. "A c-Jun dominant negative mutant protects sympathetic neurons against programmed cell death," *Neuron*. 14: 927–939, 1995; Verheij, M., Bose, R., Lin, X. H., Yao, B., Jarvis, W. D., Grant, S., Birrer, K M. J., Szabo, E., Zon, L. I., Kyriakis, J. M., Haimovitz F A., Fuks, Z., and Kolesnick, R. N. "Requirement for ceramide-initiated SAPK/JNK signalling in stress-induced apoptosis," *Nature*. 380: 75–9, 1996; Hibi, M., Lin, A., Smeal, T., Minden, A., and Karin, M. "Identification of an oncoprotein- and UV-responsive protein kinase that binds and potentiates the c-Jun activation domain," *Genes Dev*. 7: 2135–48, 1993; Derijard, B., Hibi, M., Wu, I. H., Barrett, T., Su, B., Deng, T., Karin, M., and Davis, R. J. "JNK1: a protein kinase stimulated by UV light and Ha-Ras that binds and phosphorylates the c-Jun activation domain," *Cell*. 76: 1025–37, 1994; and Chen, Y. R., Wang, X., Templeton, D., Davis, R. J., and Tan, T. H. "The role of c-Jun N-terminal kinase (JNK) in apoptosis induced by ultraviolet C and gamma radiation. Duration of JNK activation may determine cell death and proliferation," *J Biol Chem*. 271: 31929–36, 1996.

Protein tyrosine kinases (PTK) play important roles in the initiation and maintenance of biochemical signal transduction cascades that affect proliferation and survival of B-lineage lymphoid cells. Oxidative stress has been shown to activate BTK, SYK, and Src family PTK. It is known that PTK activation precedes and mandates radiation-induced activation of c-jun protooncogene expression in human B-lineage lymphoid cells (Chae, H. P., Jarvis, L. J., and Uckun, F. M. Cancer Res. 53: 447–51, 1993). However, the identity of the PTK responsible for radiation-induced c-jun activation is not yet known. See Uckun, F. M., Waddick, K.

G., Mahajan, S., Jun, X., Takata, M., Bolen, J., and Kurosaki, T. "BTK as a mediator of radiation-induced apoptosis in DT-40 lymphorna B cells," *Science.* 273: 1096–100, 1996; Kurosaki, T. "Molecular mechanisms in B cell antigen receptor signaling," *Curr Opin Immunol.* 9: 309–18, 1997; Uckun F. M., Evans W. E., Forsyth C. J., Waddick K. G., T-Ahlgren L., Chelstrom L. M., Burkhardt A., Bolen J., Myers D. E. "Biotherapy of B-cell precursor leukemia by targeting genistein to CD19-associated tyrosine kinases." *Science* 267:886–891, 1995; Myers D. E., Jun X., Waddick K. G., Forsyth C., Chelstrom L. M., Gunther R. L., Turner N. E., Bolen J., Uckun F. M. "Membrane-associated CD19-LYN complex is an endogenous p53-independent and bcl-2-independent regulator of apoptosis in human B-lineage lymphoma cells." *Proc Nat'l Acad Sci USA* 92: 9575–9579, 1995; Tuel Ahlgren, L., Jun, X., Waddick, K. G., Jin, J., Bolen, J., and Uckun, F. M. "Role of tyrosine phosphorylation in radiation-induced cell cycle-arrest of leukemic B-cell precursors at the G2-M transition checkpoint," *Leuk Lymphoma.* 20: 417–26, 1996; Qin, S., Minami, Y., Hibi, M., Kurosaki, T., and Yamamura, H. "Syk-dependent and -independent signaling cascades in B cells elicited by osmotic and oxidative stress," *J Biol Chem.* 272: 2098–103,1997; Saouaf, S. J., Mahajan, S., Rowley, R. B., Kut, S., Fargnoli, J., Burkhardt, A. L., Tsukada, S., Witte, O. N., and Bolen, J. B. "Temporal differences in the activation of three classes of non-transmembrane protein tyrosine kinases following B cell antigen receptor surface engagement," *Proc Natl Acad Sci USA.* 91: 9524–28, 1994; Law, D. A., Chan, V. F. W., Datta, S. K., and DeFranco, A. L. "B-cell antigen receptor motifs have redundant signalling capabilities and bind the tyrosine kinases PTK72,Lyn and Fyn," *Curr Biol.* 3: 645–57, 1993; Hibbs, M. L., Tarlinton, D. M., Armes, J., Grail, D., Hodgson, G., Maglitto, R., Stacker, S. A., and Dunn, A. R. "Multiple defects in the immune system of Lyn-deficient mice, culminating in autoimmune disease," *Cell.* 83: 301–311, 1995; Aoki, Y., Isselbacker, K. J., and Pilai, S. "Bruton tyrosine kinase is tyrosine phosphorylated and activated in pre-B lymphocytes and receptor-ligated B cells," *Proc Natl Acad Sci USA.* 91: 10606–10609, 1994; Jugloff, L. S. and Jongstra Bilen, J. "Cross-linking of the IgM receptor induces rapid translocation of IgM-associated Ig alpha, Lyn, and Syk tyrosine kinases to the membrane skeleton, *J Immunol.* 159: 1096–106, 1997; Thomis, D. S., Gumiak, C. B., Tivol, E., Sharpe, A. H., and Berg, L. J. "Defects in B lymphocyte maturation and T lymphocyte activation in mice lacking Jak 3," *Science.* 270: 794–797, 1995; Nosaka, T., Van Deursen, J. M., Tripp, R. A., Thierfelder, W. E., Witthuhn, B. A., McMickle, A. P., Doherty, P. c., Grosveld, G. C., and Ihle, J. N. "Defective lymphoid development in mice lacking Jak 3," *Science.* 270: 800–802, 1995.

U.S. patent application Ser. No. 09/087,479 (entitled Quinazolines For Treating Brain Tumor; filed 28 May 1998) discloses hydroxyquinazoline derivatives that exhibit potent cytotoxicity against human glioblastoma cells (i.e. brain tumor cells). Because JAK-3 is not known to be present in these glioblastoma cells, the cytotoxic activity of the hydroxyquinazoline derivatives is not believed to result from inhibition of JAK-3 activity. Additionally, the cytotoxic activity of the hydroxyquinazoline derivatives is not known to result from the inhibition of c-jun activation.

There is currently a need for therapeutic agents and methods that are useful for preventing or reducing cell damage that results from exposure to radiation and chemical agents that cause DNA-damage. There is also a need for chemical agents as well as in vitro and in vivo methods that can be used to further investigate the biological pathways associated with DNA-damage that results from exposure to radiation or chemical agents.

SUMMARY OF THE INVENTION

The invention provides a method comprising inhibiting c-jun expression in cells (e.g. mammalian or avian) by contacting the cells (in vitro or in vivo) with a substance that inhibits the activity of Janus family kinase 3 (JAK-3).

The invention also provides a therapeutic method for preventing or treating a pathological condition in a mammal (e.g. a human) wherein c-jun activation is implicated and inhibition of its expression is desired comprising administering to a mammal in need of such therapy, an effective amount of a substance that inhibits the activity of JAK-3.

The invention also provides novel compounds of formula I as well as processes and intermediates useful for their preparation.

The invention also provides substances that are effective to inhibit JAK-3 for use in medical therapy (preferably for use in treating conditions that result from exposure to radiation or to chemical agents that cause DNA damage), as well as the use of substances that inhibit JAK-3 for the manufacture of a medicament for the treatment of a condition that is associated with exposure to radiation, or to chemical agents that cause DNA damage.

Figure 4A:
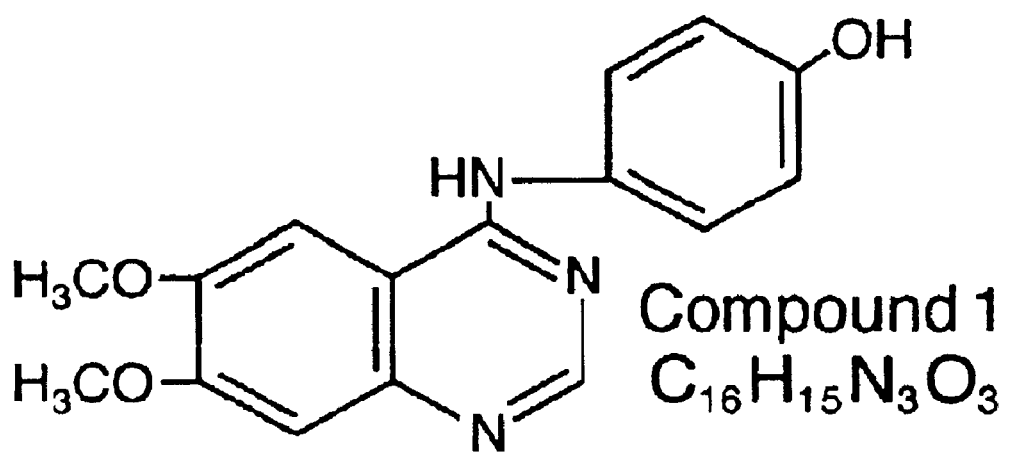
Figure 4A:
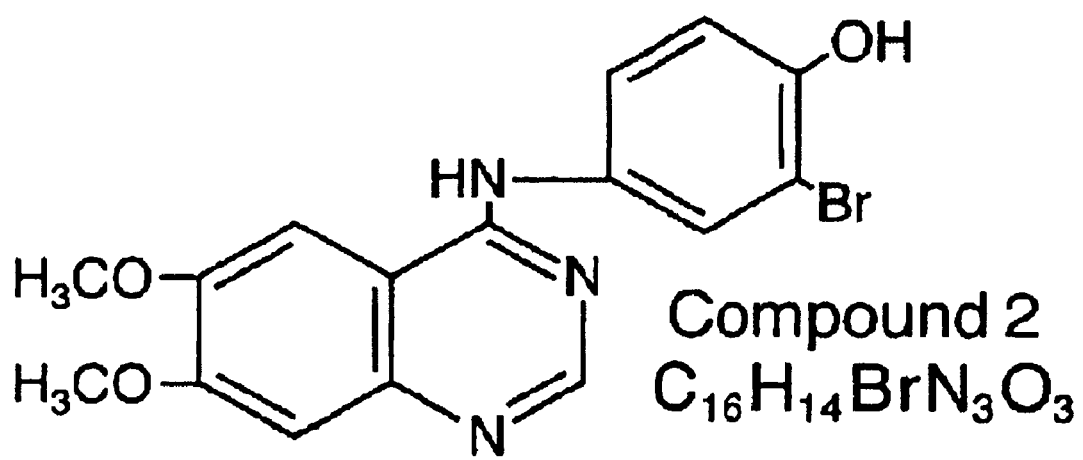
Figures 1, 4B:
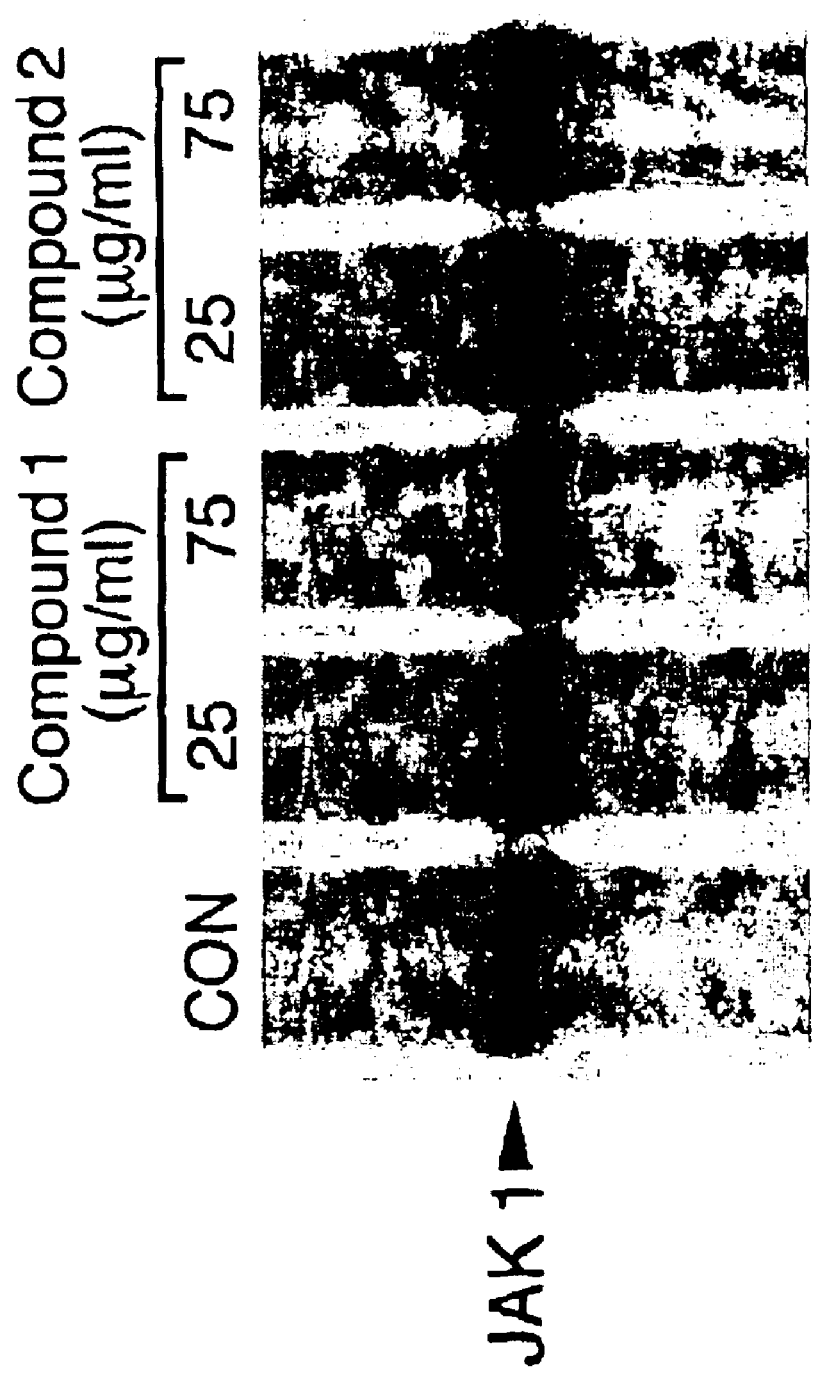

FIGS. 4B1–B4. JAK-3 Inhibitors. [A]. Structures of JAK-3 inhibitors. [B] Specificity of JAK-3 inhibitors. Sf21 cells infected with baculovirus expression vectors for JAK-1 JAK-2 or JAK-3 were subjected to immunoprecipitation with anti-JAK antibodies. JAK-1 (shown in B.1), JAK-2 (shown in B.2) and JAK-3 (shown in B.3 and B.4 which illustrate results from 2 independent experiments) immune complexes were treated with 1% DMSO (vehicle control= CON), Compound 1, or Compound 2 for 1 hour prior to hot kinase assays, as described (20,22). Both compounds inhibited JAK-3 when used at 10 µg/ml whereas they did not inhibit JAK-1 or JAK-2 even at 75 µg/ml [C]. EMSAs of 32Dc22-IL-2Rβ cells. Compound 1(100 (g/ml) and Compound 2 (100 (g/ml) inhibited IL-2 triggered JAK-3-dependent STAT activation but not IL-3-triggered JAK-1/JAK-2-dependent STAT activation in 32Dc11-IL-2Rβ cells.

Figures 2, 4B:
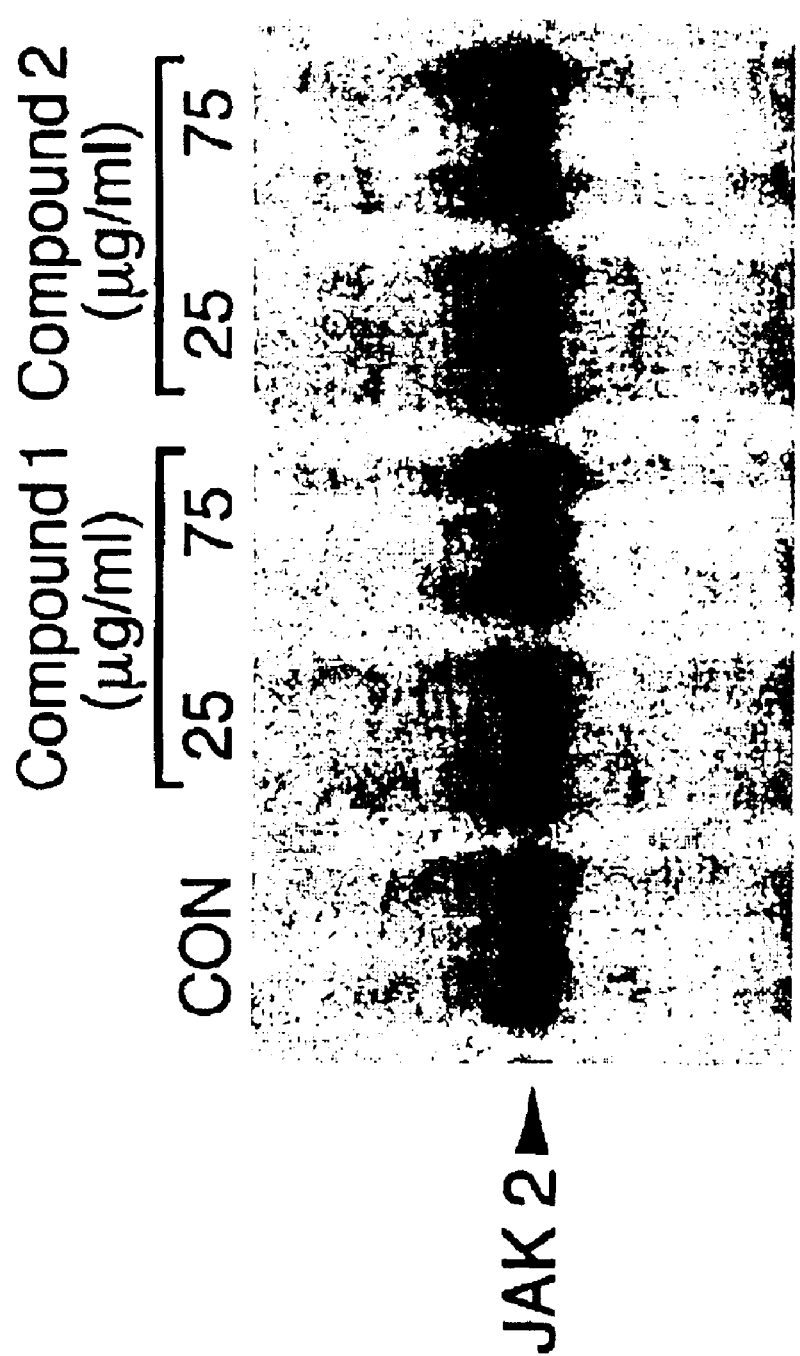
Figure 5:
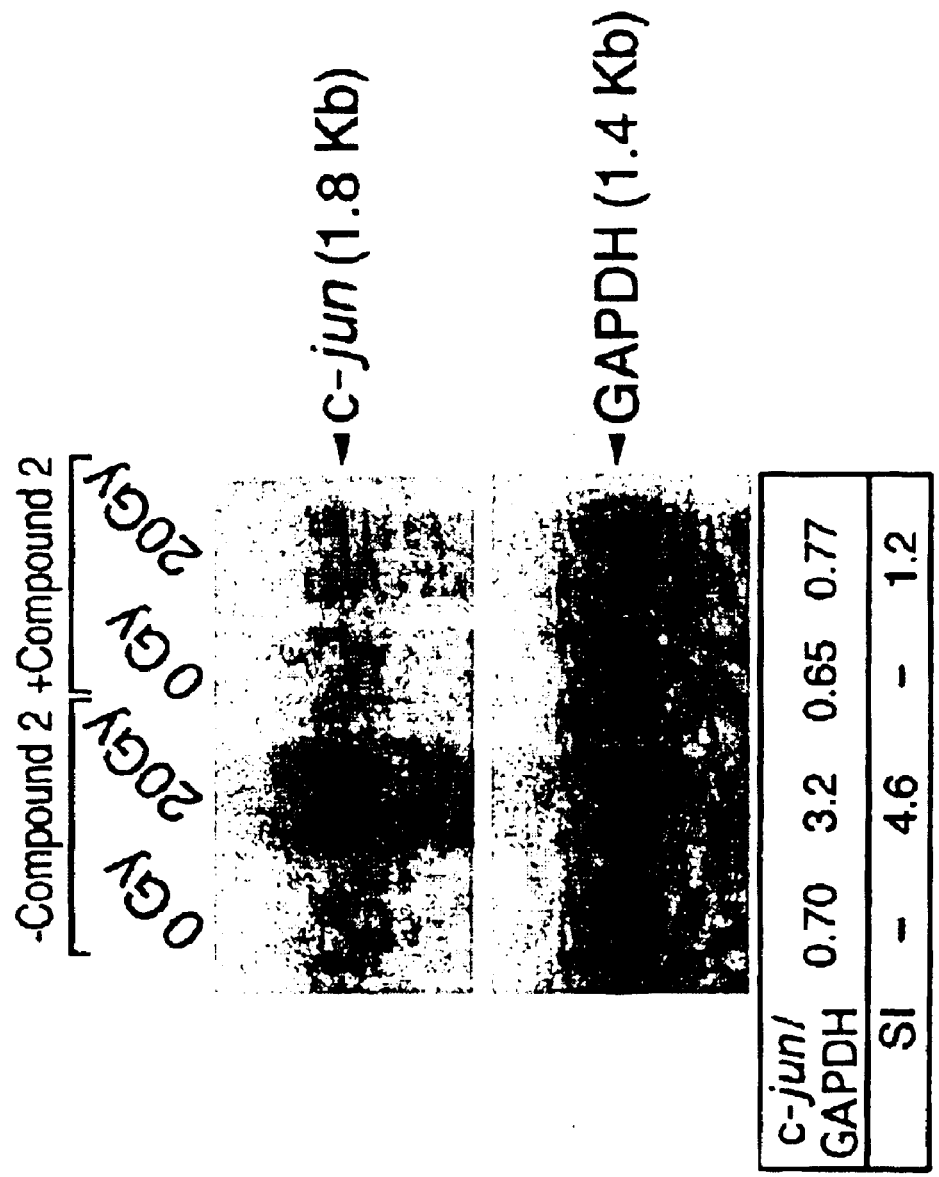

FIG. 5. Effects of a JAK-3 inhibitor on c-jun induction in irradiated DT-40 cells. Cells were treated with the quinazoline derivative 4(3'-Bromo-4'-hydroxyl-phenyl)-amino-6,7-dimethoxyquinazoline (100 mg/ml) for 24 hours at 37° C. prior to exposure to 20 Gy ionizing radiation. c-jun expression levels were determined as outlined in FIGS. 1–3.

DETAILED DESCRIPTION

As used herein, the term "inhibit" means to reduce by a measurable amount, or prevent entirely; and the phrase "inhibit c-jun activation" includes the inhibition of RNA production and the inhibition of the production of the protein encoded by the RNA.

Applicants examined the potential involvement of BTK, SYK and LYN in radiation-induced c-jun activation, using DT-40 chicken lymphoma B-cell clones rendered deficient for these specific PTK by targeted gene disruption. It was found that BTK plays no role in radiation-induced c-jun activation. Similarly, neither LYN nor SYK are required for activation of c-jun after radiation exposure. However, their participation may influence the magnitude of the c-jun response. It was unexpectedly discovered, however, that an inhibitor of Janus family kinase 3 (JAK-3) abrogated radiation-induced c-jun activation.

C-jun expression can be activated by exposure to chemical agents that damage DNA such as ara-C, a topoisomerase II inhibitors, or alkylating agents. C-jun activation can also result from exposure to ultraviolet radiation or ionizing radiation. According to the invention, inhibitors of JAK-3 can be used to inhibit c-jun expression resulting from exposure to radiation or exposure to chemical agents.

The methods of the invention can be carried out in vitro. Such in vitro methods are also useful for studying the biological processes associated with cell response to DNA damaging agents. The methods of the invention can also be carried out in vivo. Such methods can also be used to study the biological processes associated with cell response to DNA damaging agents, as well as for treating pathological conditions in mammals (e.g. humans) that result from exposure to DNA-damaging agents.

Pathological conditions that result from exposure to DNA-damaging agents include conditions that result from oxidative stress, such as tissue or organ (e.g. heart, liver, or kidney) damage, inflammation, and hair loss, as well as the negative effects that are produced by oxygen free radicals during chemotherapy. Oxidative stress may result from exposure to external agents, or may result from internal processes. Thus, JAK-3 inhibitors are also useful for treating conditions resulting from the action of internally generated oxygen free radicals, such as aging and amyelotrophic lateral sclerosis (ALS).

According to the invention, the JAK-3 inhibitors may be administered prophylactically, i.e. prior to exposure to the DNA-damaging agent, or the JAK-3 inhibitors may be administered after exposure to the DNA damaging agent.

The JAK-3 inhibitors useful in the methods of the invention include all compounds capable of inhibiting the activity of JAK-3, it being well known in the art how to measure a compounds ability to inhibit JAK-3, for example, using standard tests similar to the test described hereinbelow in Example 2 under the heading "Effects of a JAK-3 inhibitor on radiation-induced c-jun activation in DT40 cells."

JAK-3 inhibitors that are useful in the methods of the invention include compounds of formula I:

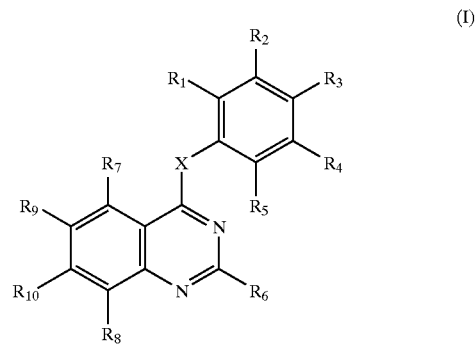

(I)

wherein
X is HN, $R_{11}N$, S, O, $CH_2$, or $R_{11}CH$;
$R_{11}$ is hydrogen, $(C_1-C_4)$alkyl, or $(C_1-C_4)$alkanoyl;
$R_1-R_8$ are each independently hydrogen, hydroxy, mercapto, amino, nitro, $(C_1-C_4)$alkyl, $(C_1-C_4)$alkoxy, $(C_1-C_4)$alkylthio, or halo; wherein two adjacent groups of $R_1-R_5$ together with the phenyl ring to which they are attached may optionally a form a fused ring, for example forming a naphthyl or a tetrahydronaphthyl ring; and further wherein the ring formed by the two adjacent groups of $R_1-R_5$ may optionally be substituted by 1, 2, 3, or 4 hydroxy, mercapto, amino, nitro, $(C_1-C_4)$alkyl, $(C_1-C_4)$alkoxy, $(C_1-C_4)$alkylthio, or halo; and
$R_9$ and $R_{10}$, are each independently hydrogen, $(C_1-C_4)$alkyl, $(C_1-C_4)$alkoxy, halo, or $(C_1-C_4)$alkanoyl; or $R_9$ and $R_{10}$ together are methylenedioxy; or a pharmaceutically acceptable salt thereof.

The following definitions are used, unless otherwise described: halo is fluoro, chloro, bromo, or iodo. Alkyl, alkanoyl, etc. denote both straight and branched groups; but reference to an individual radical such as "propyl" embraces only the straight chain radical, a branched chain isomer such as "isopropyl" being specifically referred to. $(C_1-C_4)$Alkyl includes methyl, ethyl, propyl, isopropyl, butyl, iso-butyl, and sec-butyl; $(C_1-C_4)$alkoxy includes methoxy, ethoxy, propoxy, isopropoxy, butoxy, iso-butoxy, and sec-butoxy; and $(C_1-C_4)$alkanoyl includes acetyl, propanoyl and butanoyl.

A specific group of compounds are compounds of formula I wherein $R_1-R_5$ are each independently hydrogen, mercapto, amino, nitro, $(C_1-C_4)$alkyl, $(C_1-C_4)$alkoxy, $(C_1-C_4)$alkylthio, or halogen.

Another specific group of compounds are compounds of formula I wherein $R_9$ and $R_{10}$ are each independently hydrogen, $(C_1-C_4)$alkyl, halo, or $(C_1-C_4)$alkanoyl; or $R_9$ and $R_{10}$ together are methylenedioxy; or a pharmaceutically acceptable salt thereof.

JAK-3 inhibitors that are useful in the methods of the invention also include compounds of formula I as described in U.S. patent application Ser. No. 09/087,479 (entitled Quinazolines For Treating Brain Tumor; filed 28 May 1998).

Preferred JAK-3 inhibitors include 4-(4'-hydroxylphenyl)-amino-6,7-dimenthoxyquinazoline and 4-(3'-bromo4'-hydroxylphenyl)-amino-6,7-dimethoxyquinazoline, or a pharmaceutically acceptable salt thereof.

Substances that inhibit JAK-3 ("the Substance(s)") can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the Substances may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the Substance may be combined with one or more excipients and used in the form of ingestible tablets, buccal tablets, troches, capsules, elixirs, suspensions, syrups, wafers, and the like. Such compositions and preparations should contain at least 0.1% of the Substance. The percentage of the compositions and preparations may, of course, be varied and may conveniently be between about 2 to about 60% of the weight of a given unit dosage form. The amount of Substance in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the Substance may be incorporated into sustained-release preparations and devices.

The Substances may also be administered intravenously or intraperitoneally by infusion or injection. Solutions of the Substance can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the Substance which are adapted for the extemporaneous preparation of sterile injectable or infusible solutions or dispersions, optionally encapsulated in liposomes. In all cases, the ultimate dosage form must be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the Substance in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the Substances may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the Substances can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the Substances to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the Substance in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%.

The amount of the Substance required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The Substance is conveniently administered in unit dosage form; for example, containing 5 to 1000 mg, conveniently 10 to 750 mg, most conveniently, 50 to 500 mg of active ingredient per unit dosage form.

Ideally, the Substance should be administered to achieve peak plasma concentrations of from about 0.5 to about 75 $\mu$M, preferably, about 1 to 50 $\mu$M, most preferably, about 2 to about 30 $\mu$M. This may be achieved, for example, by the intravenous injection of a 0.05 to 5% solution of the Substance, optionally in saline, or orally administered as a bolus containing about 1–100 mg of the Substance. Desirable blood levels may be maintained by continuous infusion to provide about 0.01–5.0 mg/kg/hr or by intermittent infusions containing about 0.4–15 mg/kg of the Substance.

The Substance may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The invention will now be illustrated by the following non-limiting Examples.

EXAMPLES

Example 1
Chemical synthesis and Characterization of JAK-3 Inhibitors

Melting points are uncorrected. $^1$H NMR spectra were recorded using a Varian Mercury 300 spectrometer in DMSO-$d_6$ or CDCl$_3$. Chemical shifts are reported in parts per million (ppm) with tetramethylsilane (TMS) as an internal standard at zero ppm. Coupling constant (J) are given in hertz and the abbreviations s, d, t, q, and m refer to singlet, doublet, triplet, quartet and multiplet, respectively. Infrared spectra were recorded on a Nicolet PROTEGE 460-IR spectrometer. Mass spectroscopy data were recorded on a FINNIGAN MAT 95, VG 7070E-HF G.C. system with an HP 5973 Mass Selection Detector. UV spectra were recorded on BECKMAN DU 7400 and using MeOH as the solvent. TLC was performed on a precoated silica gel plate (Silica Gel KGF; Whitman Inc). Silica gel (200–400 mesh, Whitman, Inc.) was used for all column chromatography separations. All chemicals were reagent grade and were purchased from Aldrich Chemical Company (Milwaukee, Wis.) or Sigma Chemical Company (St. Louis, Mo.).

The common synthetic precursor 4-chloro-6,7-dimethoxyquinazoline (7), used for preparing compounds (1) and (2), was prepared using liturature procedures as illustrated in Scheme 1.

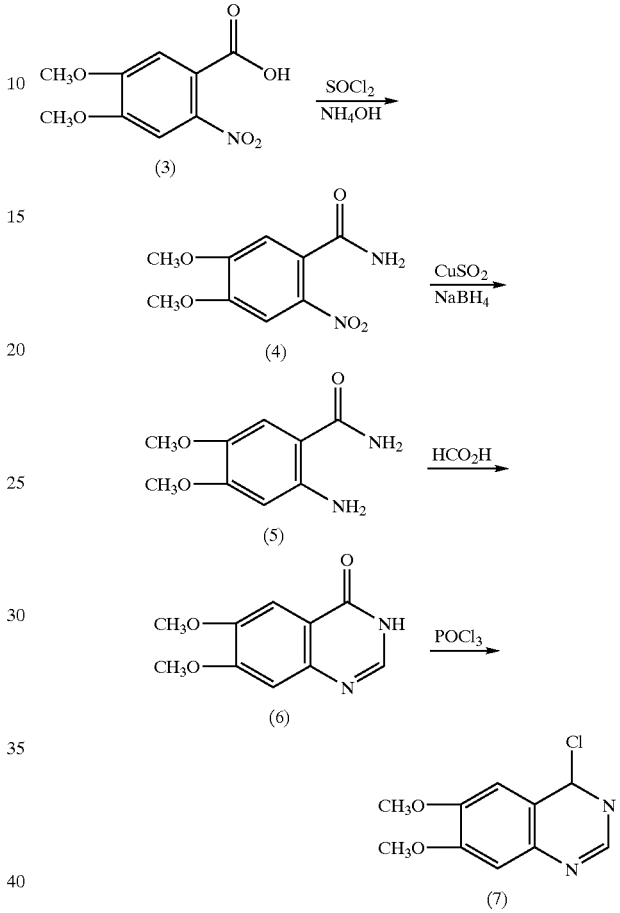

4,5-Dimethoxy-2-nitrobenzoic acid (3) was treated with thionyl chloride and then reacted with ammonia to give 4,5-dimethoxy-2-nitrobenzamide (4) as described by F. Nomoto et al. Chem. Pharm. Bull. 1990, 38, 1591–1595. The nitro group in compound (4) was reduced with sodium borohydride in the presence of copper sulfate (see C. L. Thomas *Catalytic Processes and Proven Catalysts* Academic Press, New York (1970)) to give 4,5-dimethoxy-2-aminobenzamide (5) which was cyclized by refluxing with formic acid to give 6,7-dimethoxyquinazoline-4(3H)-one (6). Compound (6) was refluxed with phosphorus oxytrichloride to provide the common synthetic precursor (7).

Compounds 1 and 2 (FIG. 4) were prepared from the common synthetic precursor (7) and the requsite aniline as follows.

4-(4'-Hydroxylphenyl)-amino-6,7-dimethoxyquinazoline (1). A mixture of 448 mg (2 mmol) of 4-chloro-6,7-dimethoxyquinazoline (7) and 2.5 mmol of 4-hydroxyaniline in 20 ml of alcohol (EtOH or MeOH) was refluxed for 8 hours. After cooling triethylamine was added to basify the solution, and the solvent was concentrated to give material that was recrystallized from DMF to give compound (1); 84.29%; m.p. 245.0–248.0° C.; $^1$H NMR (DMSO-$d_6$): δ 11.21(s, 1H, —NH), 9.70(s, 1H, —OH), 8.74(s, 1H, 2-H), 8.22(s, 1H, 5-H), 7.40(d, 2H, J=8.9 Hz, 2',6'-H), 7.29(s, 1H, 8-H), 6.85(d, 2H, J=8.9 Hz, 3',5'-H), 3.98(s, 3H, —OCH$_3$), 3.97(s, 3H, —OCH$_3$). UV(MeOH) $\lambda_{max}$(e): 203.0, 222.0, 251.0, 320.0 nm. IR(KBr)u$_{max}$: 3428, 2836, 1635, 1516, 1443, 1234 cm$^{-1}$.GC/MS m/z 298 (M$^+$+1, 100.00), 297(M$^+$, 26.56), 296(M$^+$–1, 12.46).

4-(3'-Bromo-4'-hydroxylphenyl)-amino-6,7-dimethoxy-quinazoline (2). A mixture of 448 mg (2 mmol) of 4-chloro-6,7-dimethoxy-quioazoline (7) and 2.5 mmol of 3-bromo-4-hydroxyaniline in 20 ml of alcohol (EtOH or MeOH) was refluxed for 8 hours. After cooling, triethylamine was added to basify the solution, and the solvent was concentrated to give material that was recrystallized from DMF to give compound (2); 89.90%; m.p. 233.0–233.5° C.; $^1$H NMR (DMSO-d$_6$): δ 10.08(s, 1H, —NH), 9.38(s, 1H, —OH), 8.40(s, 1H, 2-H), 7.89(d, 1H, J$_{2',5'}$=2.7 Hz, 2'-H), 7.75(s, 1H, 5-H), 7.55(dd, 1 H, J$_{5',6'}$=9.0 Hz, J$_{2',6'}$=2.7 Hz, 6'-H), 7.14(s, 1H, 8-H), 6.97(d, 1H, J$_{5',6'}$=9.0 Hz, 5'-H), 3.92(s, 3H, —OCH$_{ER}$), 3.90(s, 3H, —OCH$_3$). UV(MeOH)$\lambda_{max}$(e): 203.0, 222.0, 250.0, 335.0 nm. IR(KBr)u$_{max}$: 3431(br), 2841, 1624, 1498, 1423, 1244 cm$^{-1}$. GC/MS m/z 378( M$^+$ +2, 90.68), 377(M$^+$ +1,37.49), 376(M$^+$, 100.00), 360(M$^+$ 3.63), 298(18.86), 282 (6.65).

Example 2

Biological Screening

Materials and Methods

Cell Lines.

The establishment and characterization of BTK-deficient, SYK-deficient, and LYN-deficient clones and reconstituted SYK-deficient cell lines of DT-40 chicken lymphoma B-cells were previously reported. The culture medium was RPMI 1640 (Life Technologies; Gaithersburg, Md.), supplemented with 1% chicken serum (Sigma; St. Louis, Mo.), 5% fetal bovine serum (Hyclone, Logan,Utah) and 1% penicillin-streptomycin (Life Technologies). See Uckun, F. M., Waddick, K. G., Mahajan, S., Jun, X., Takata, M., Bolen, J., and Kurosaki, T. *Science*. 273: 1096–100, 1996; Kurosaki, T. *Curr Opin Immunol.* 9: 309–18, 1997; Kurosaki, T., Johnson, S. A., Pao, L., Sada, K., Yamamura, H., and Cambier, J. C. *J. Exp. Med.* 182: 1815–1823, 1995; and Dibirdik I., Kristupaitis D., Kurosaki T., Tuel-Ahlgren L., Chu A., Pond D., Tuong D., Luben R., Uckun F. M. *J Biol. Chem.* 273(7), pp:4035–4039, 1998.

Use of PTK Inhibitors.

Cells (2×10$^6$/ml) were treated for 24 hours at 37° C. with either (1) the PTK inhibitory isoflavone genistein (Calbiochem, La Jolla, Calif.) at 111 mM (30 mg/ml) concentration or (2) the Janus family kinase, 3 (JAK-3)-specific PTK inhibitor 4-(3'-bromo-4'-hydroxyphenyl)-amino-6,7-dimethoxyquinazoline, C$_{16}$H$_{14}$Br(N$_3$O$_3$), kindly provided by Dr. Xing-Ping Liu, Alexander and Parker Pharmaceutical Inc., Roseville, Minn.) at 270 mM (100 mg/ml) prior to radiation in order to assess the effects of these agents on radiation-induced c-jun activation.

Irradiation of cells.

Cells (2×10$^6$ cells/ml) in plastic tissue culture flasks were irradiated with 10–20 Gy at a dose rate of 4 Gy/min during log phase growth and under aerobic conditions using a $^{137}$CS irradiator (J. L. Shephard, Glendale, Calif., as previously described by Tuel Ahlgren, L., Jun, X., Waddick, K. G., Jin, J., Bolen, J., and Uckun, F. M. "Role of tyrosine phosphorylation in radiation-induced cell cycle-arrest of leukemic B-cell precursors at the G2-M transition checkpoint," *Leuk Lymphoma*. 20: 417–26, 1996; and Uckun, F. M., Jaszcz, W., Chandan Langlie, M., Waddick, K. G., Gajl Peczalska, K. and Song, C. W. "Intrinsic radiation resistance of primary clonogenic blasts from children with newly diagnosed B-cell precursor acute lymphoblastic leukemia," *J Clin Inves.* 91:1044–1051, 1993. In some experiments, cells were preincubated with PTK inhibitors for 24 hours prior to irradiation.

c-jun probe.

A 506 basepair (bp) c-jun probe was obtained by polymerase chain reaction (PCR) amplification of chicken genomic DNA. Primer sequences were determined based upon the sequence of chicken c-jun (GenBank accession code CHKJUN). Two primers: 5'-ACTCTGCACC CAACTACAACGC-3' (SEQ. ID NO: 1) and 5'-CTTCTACCGT CAGCTTTACGCG-3' (SEQ ID NO: 2) were used for amplification. Amplification was performed with a mix of Taq polymerase and a proof reading polymerase (eLONGase:Taq polymerase plus Pyrococcus species GB-D polymerase, Gibco BRL, Grand Island, N.Y.) on an thermocycler, Ericomp Delta II cycler, using a hot start. PCR products were subsequently cloned into the cloning vector, PCR 2.1 (Invitrogen, San Diego, Calif.). An insert of the proper size (506 basepair) was identified as chicken c-jun by sequence analysis using PRISM dye terminator cycle sequencing (AmpliTaq® DNA Polymerase, FS) and analyzed on an automated sequencer, ALF express sequencer (Pharmacia Biotech, Piscataway, N.J.). A 538 base pair chicken glyceraldehyde 3-phosphate dehydrogenase (GAPDH) probe was generated by reverse transcription and subsequent PCR amplification (RT-PCR) from chicken RNA with the following primers: 5'-AGAGGTGCTGCCCAGAACATCATC-3' (SEQ ID NO: 3) and 5'-GTGGGGAGACAGAAGGGAACAGA-3' (SEQ ID NO: 4). A 413 bp chicken B-actin probe was generated by RT-PCR amplification from chicken RNA with the following primers: 5'-GCCCTCTTCCAGCATCTTTCTT-3' (SEQ ID NO: 5) and 5'-TTTATGCGCATTTATGGGTT-3' (SEQ ID NO: 6). The amplified cDNAs were cloned into PCR 2.1.

RNA isolation and Northern blot hybridization analysis.

Total RNA was extracted from approximately 2.5×10$^7$ cells with Trizol Reagent, a monophasic solution of phenol and guanidine isothiocyanate as described by Chomcznski, P. and Sacchi, N. "Single-step method of RNA isolation by guanidinium-thiocyanate-phenol-chloroform extraction," *Anal. Biochem.* 162: 156–159, 1987. Poly (A)$^+$RNA was isolated directly from 1–3×10$^8$ cells with an Invitrogen Fast Trak 2.0 mRNA isolation kit. In brief, cells were lysed in a sodium dodecyl sulfate (SDS) lysis buffer containing a proprietary mixture of proteases. The lysate was directly incubated with oligo-dT for absorption and subsequent elution of poly (A)$^+$RNA.

Two micrograms of poly (A)$^+$or 20 micrograms of total RNA were denatured in formaldehyde/formamide loading dye at 65° prior to loading onto a 1% agarose-formaldehyde denaturing gel. Transcript sizes were determined relative to RNA markers of 0.5–9 kb. The gels were stained with Radiant Red in H$_2$O check loading and integrity of RNA prior to transfer. The RNA was subsequently transferred to positively charged nylon membrane with 20× standard sodium citrate(SSC) transfer buffer (1×SSC=0.15 M sodium chloride-0.015 M sodium citrate) by downward capillary transfer. The c-jun fragment was radiolabeled by random priming with [(–$^{32}$P]-dCTP (3000 Ci/mM) [Amersham, Arlington Heights, Ill.] (40). Northern blots were hybridized overnight at 42° C. in prehybridization/hybridization solution (50% formamide with proprietary blocking and background reduction reagents; Ambion, Austin, Tex.) for 16–24 hours and unbound probe was removed by washing to a final stringency of 0. 1% SDS, 0.1×SSC (65° C.). The blots were analyzed both by autoradiography and using the BioRad Storage Phosphor Imager System (BioRad, Hercules, Calif.) for quantitative scanning. The blots were subsequently stripped in boiling 0.1% SDS, and then rehybridized with a chicken GAPDH and/or chicken ($\beta$-actin probe to normalize for loading differences.

Results and Discussion

Exposure of DT40 chicken lymphoma B-cells to ionizing radiation activates the c-jun protooncogene.

Figure 1A:
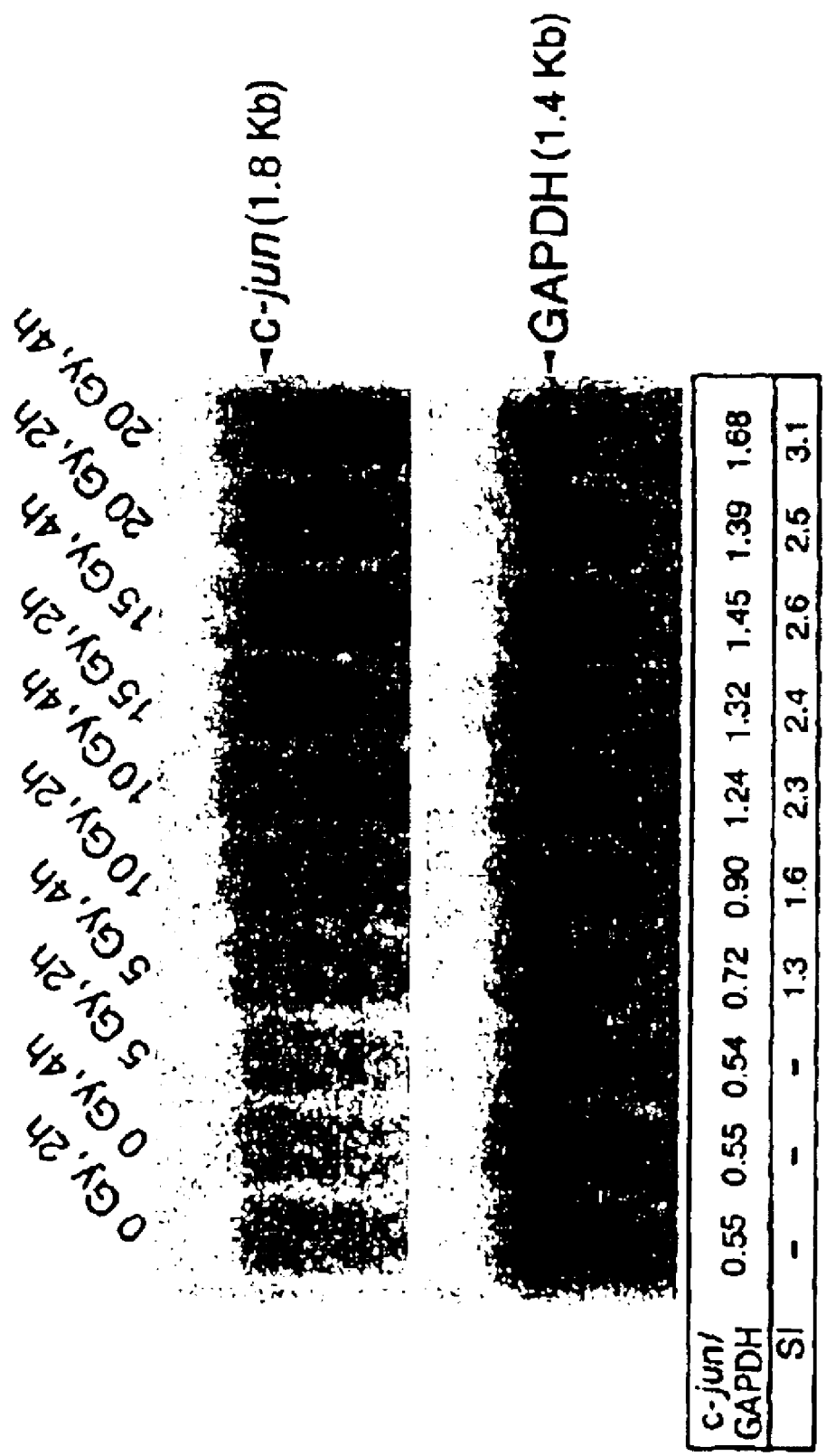
FIGS. 1A and 1B. Radiation-induced c-jun activation in wild-type DT-40 lymphoma B-cells. [A]. Dose reponse for induction of c-jun mRNA. DT-40 chicken cells were irradiated at the indicated doses (0, 10, 15, 20 Gy). Total RNA was extracted after a 2 hours or 4 hours post-irradiation time period. RNA (20 mg) was loaded on a Northern gel and transferred by capillary blotting to a nylon membrane. The Northern blot was hybridized with a $^{32}$P labeled chicken c-jun probe (top panel) or a chicken GAPDH probe (bottom panel). The inset shows the values for the c-jun/GAPDH transcript expression ratios as determined with a Bio Rad Storage Phosphor Imager and corresponding SI values [B]. Effect of the PTK inhibitor genistein on induction of c-jun mRNA. Cells were treated with 30 mg/ml of genistein for 24 hours at 37° C. prior to exposure to 20 Gy ionizing radiation. c-jun expression levels were determined as in [A].

Exposure of human lymphoma B-cells to 10–20 Gy-rays results in enhanced c-jun expression with a maximum response at 1–2 hours (Chae, H. P., Jarvis, L. J., and Uckun, F. M. *Cancer Res.* 53: 447–51, 1993). It has also been reported that ionizing radiation triggers in DT-40 chicken lymphoma B-cells biochemical and biological signals similar to those in human lymphoma B-cells (Uckun, F. M., Waddick, K. G., Mahajan, S., Jun, X., Takata, M., Bolen, J., and Kurosaki, T. *Science.* 273: 1096–100, 1996). In order to determine if DT-40 chicken lymphoma B-cells show a similar c-jun response to ionizing radiation, DT-40 cells were irradiated with 5,10,15 or 20 Gy and examined total RNA harvested from cells 2 or 4 hours after radiation exposure for expression levels of 1.8 kb chicken c-jun transcripts by quantitative Northern blot analysis. As shown in FIG. 1A, radiation exposure increased the level of c-jun transcripts in a dose-and time-dependent manner without significantly affecting the GAPDH transcript levels with a maximum stimulation index (SI) [as determined by comparison of the c-jun/GAPDH ratios in non-irradiated versus irradiated cells] of 3.1, 4 hours after 20 Gy. In seven additional independent experiments, the stimulation index for 20 Gy ionizing radiation at 2 hours after radiation exposure ranged from 2.4 to 3.8 (mean ( SE=2.9±0.4).

Figure 1B:
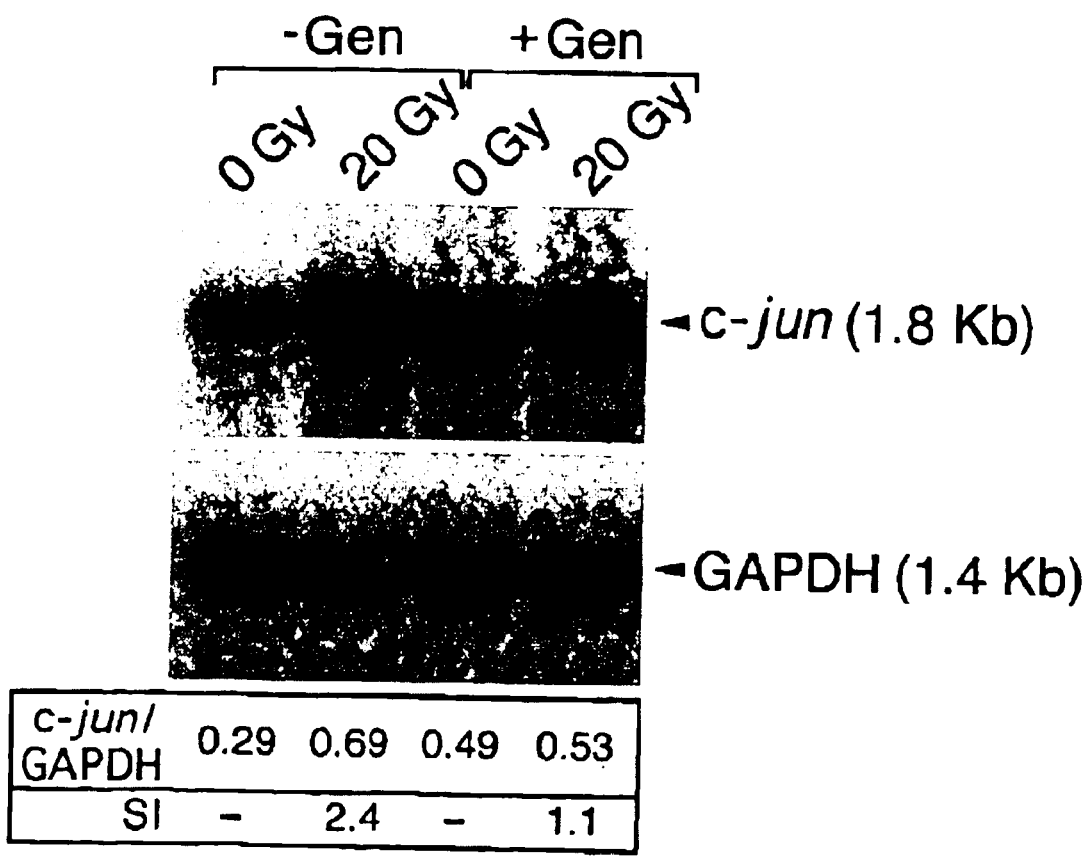
Figure 2A:
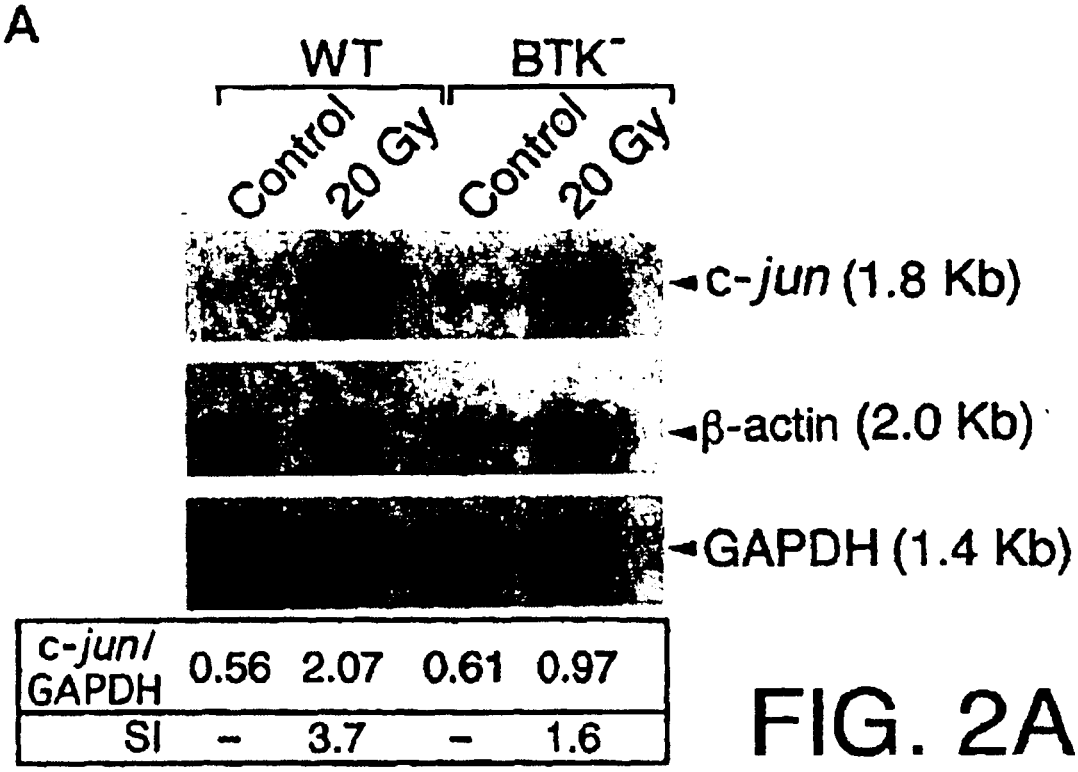
FIGS. 2A and 2B. Radiation-induced activation of c-jun in BTK⁻DT-40 cells. Two representative experiments (shown in [A] and [B]) showing induction of c-jun mRNA expression by ionizing radiation in wild type (WT) and BTK⁻DT-40 cells. Poly (A)⁺RNA was isolated from non-irradiated cells as well as irradiated cells (20 Gy, with a 2 hours post-radiation recovery period). Northern blots of 2 mg of poly (A)⁺were hybridized with c-jun probe (top panel), (-actin probe (middle panel in [A] only), and GAPDH probe (bottom panel). The inset below each panel shows the relative expression of c-jun normalized for RNA load (c-jun/GAPDH ratio) and SI (fold induction over non-irradiated controls).
Figure 2B:
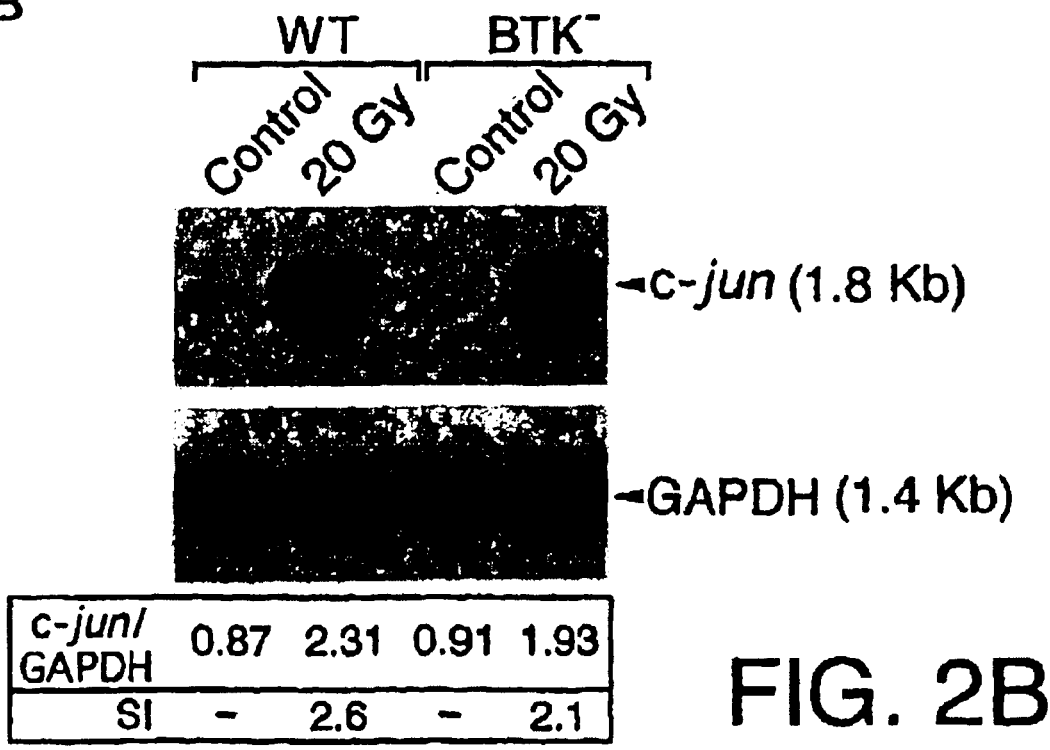

The role of PTK in radiation-induced activation of c-jun expression in chicken lymphoma B cells was examined next, since PTK inhibitors were shown to prevent radiation-induced c-jun activation in human lymphoma B-cells. As shown in FIG. 1B, ionizing radiation did not significantly enhance c-jun expression levels in DT-40 cells treated with the PTK-inhibitory isoflavone, genistein (stimulation index= 1.1) indicating that activation of a PTK is required for radiation-induced c-jun expression in chicken lymphoma B cells as well. These findings established DT-40 chicken lymphoma B-cells as a suitable model to further elucidate the molecular mechanism of radiation-induced c-jun activation.

Cytoplasmic protein tyrosine kinases BTK, LYN, and SYK are not required for radiation induced c-jun activation.

BTK is abundantly expressed in lymphoma B-cells and its activation has been shown to be required for radiation-induced apoptosis of DT-40 cells (Uckun, F. M., Waddick, K. G., Mahajan, S., Jun, X., Takata, M., Bolen, J., and Kurosaki, T. *Science.* 273: 1096–100, 1996). DT-40 cells rendered BTK-deficient by targeted disruption of the BTK genes do not undergo apoptosis after radiation exposure. Therefore, we set out to determine if BTK could be the PTK responsible for radiation-induced c-jun activation as well, by comparing the levels of c-jun induction in BTK-deficient (BTK$^-$) versus wild-type DT-40 cells. Contrary to our expectations, 20 Gy ionizing radiation did not fail to induce c-jun expression in BTK-deficient DT-40 cells in any of the three independent experiments performed. The stimulation indices ranged from 1.6 to 3.9 (mean±SE=2.4±0.5) (FIG. 2). Thus, ionizing radiation-induced increases in c-jun transcript levels do not depend upon the presence of BTK.

Figure 3A:
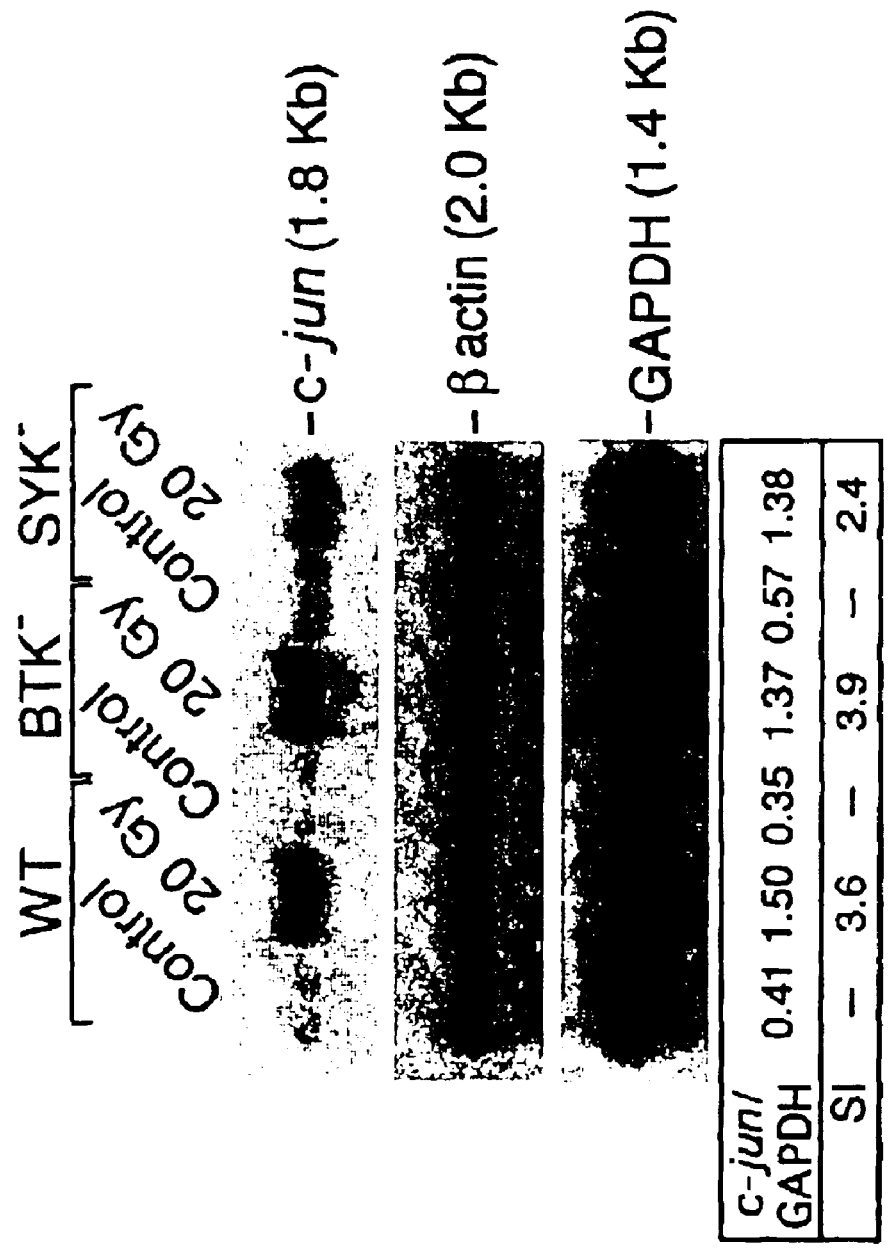
FIGS. 3A and 3B. Induction of c-jun mRNA expression by ionizing radiation in wild type and mutant DT-40 cell lines. DT-40, BTK⁻DT-40, SYK⁻DT-40 (shown in [A]), as well as LYN⁻DT-40 and LYN⁻SYK⁻DT 40 cells (shown in [B]) were irradiated with 20 Gy and poly (A)⁺RNA (in [A]) or total RNA (in [B]) was harvested after a 2 hour recovery period. RNA from non-irradiated cells was used as a control. Northern blots containing 2 mg of poly (A)⁺(in [A]) or 20 mg of total RNA (in [B]) from each cell line were hybridized with both $^{32}$P labeled c-jun probe (top panel) and GAPDH probe (bottom panel). The insets below the panels show the relative expression of c-jun normalized for RNA loading (c-jun/GAPDH ratios) as well as the SI (fold induction over non-irradiated controls).

Since SYK is also abundantly expressed in DT-40 cells and is rapidly activated after ionizing radiation, we next examined if SYK might be the PTK responsible for radiation-induced increases in c-jun transcript levels. As shown in FIG. 3A, 20 Gy ionizing radiation enhanced c-jun expression in SYK DT-40 cells rendered SYK-deficient by targeted gene disruption even though the stimulation indices observed in five independent experiments were lower than from those in wild-type cells (1.9±0.2, vs 2.9±0.4,p<0.01). Thus, SYK is not required for radiation-induced c-jun activation in DT-40 cells but it may participate in generation of an optimal signal.

Figure 3B:
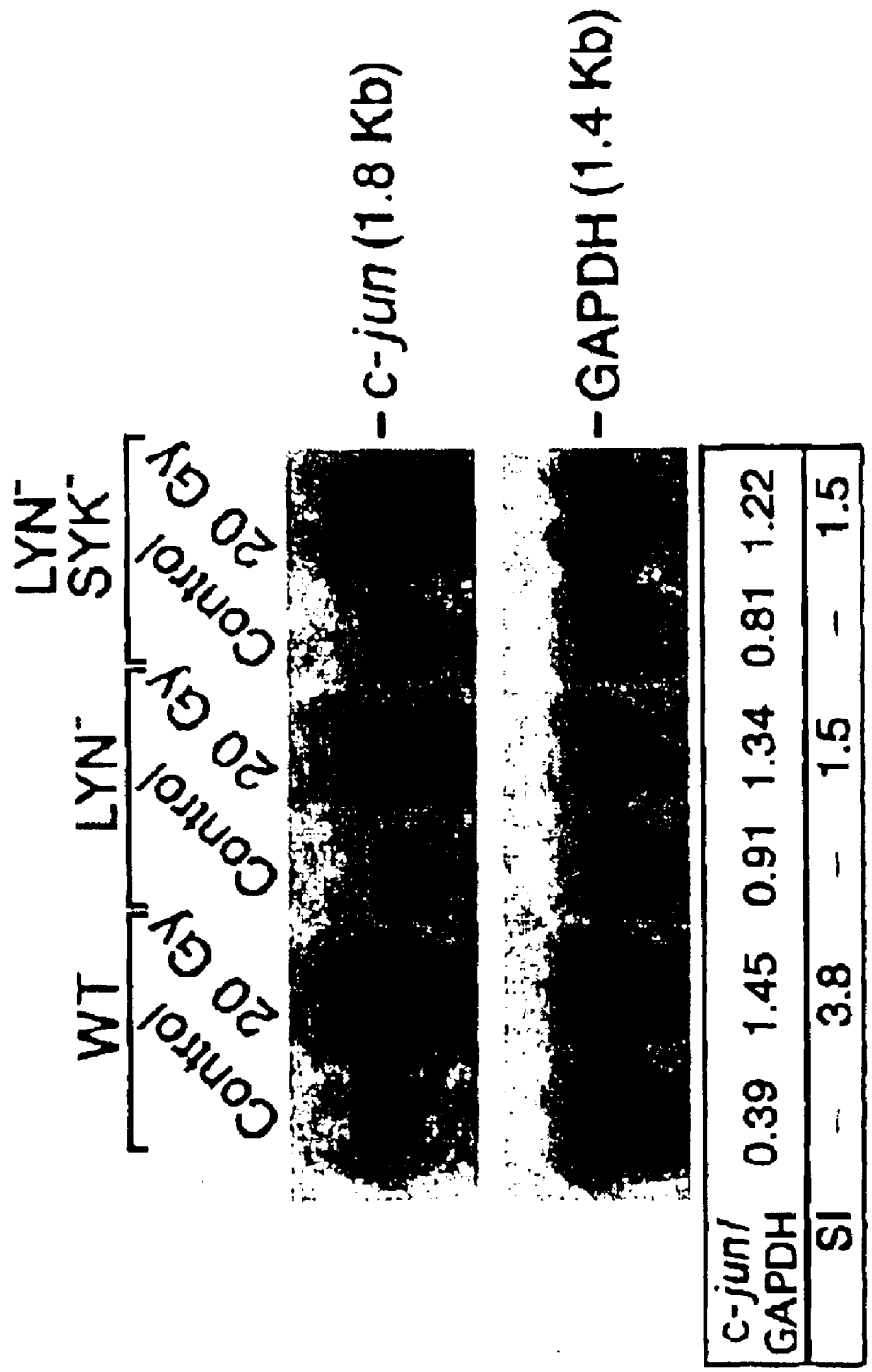

DT-40 cells express high levels of LYN but do not express other members of the Src PTK family, including BLK, HCK, SRC, FYN, or YES at detectable levels (see Uckun, F. M., Waddick, K. G., Mahajan, S., Jun, X., Takata, M., Bolen, J., and Kurosaki, T. *Science.* 273: 1096–100, 1996; Kurosaki, T., Johnson, S. A., Pao, L., Sada, K., Yamamura, H., and Cambier, J. C. "Role of the Syk autophosphorylation site and SH2 domains in B cell antigen receptor signaling," *J. Exp. Med.* 182: 1815–1823, 1995; and Takata, M., Homma, Y., and Kurosaki, T. "Requirement of phospholipase C-$\gamma$2 activation in surface immunoglobulin M-induced B cell apoptosis.," *J Exp Med.* 182: 907–914, 1995. Since it has previously been demonstrated that SRC family PTK are essential for UV-stimulated increases in c-jun expression, we postulated that the predominant SRC-family member, LYN, might mediate radiation-induced c-jun expression in DT-40 cells. To test this hypothesis, we examined the ability of ionizing radiation to activate c-jun expression in DT-40 cells rendered LYN-deficient by targeted gene disruption. LYN-deficient (LYN$^-$) cells showed enhanced c-jun expression after irradiation, however the stimulation indices were lower than those in wild-type DT-40 (FIG. 3B). Since LYN and SYK have been shown to cooperate in the generation of other signals in B-cells (see Kurosaki, T. "Molecular mechanisms in B cell antigen receptor signaling," *Curr Opin Immunol.* 9: 309–18, 1997), the ability of ionizing radiation to induce c-jun expression in LYN$^-$SYK$^-$DT-40 cells, generated by targeted disruption of the syk gene in LYN$^-$ deficient DT-40 cells was examined. As shown in FIG. 3B, LYN$^-$SYK$^-$DT-40 cells showed elevated c-jun transcript levels after irradiation, indicating that the c-jun response does not depend on either of these PTK, either alone or in cooperation. Similar to SYK, LYN is not required for radiation-induced c-jun activation in DT-40 cells but it may participate in generation of an optimal response.

Interestingly, in four independent experiments, we observed higher baseline expression levels of c-jun in SYK$^-$ DT-40 cells than in wild-type DT-40 cells (Range: 1.4–2.3-fold, mean±SE=1.6±0.2-fold), suggesting that Syk may be involved in regulation of baseline c-jun levels. To further explore this possibility, we compared c-jun levels in SYK$^-$ cells to those of SYK$^-$cells reconstituted with wild-type or kinase domain mutant (K$^-$) syk gene. We observed that reconstitution with wild-type syk reduced the higher baseline expression levels of c-jun in SYK$^-$cells, whereas reconstitution with a K$^-$syk failed to reduce c-jun levels (data not shown). These results implicate SYK as a negative regulator of c-jun expression. This novel function of SYK seems to depend on its kinase domain.

Effects of a JAK-3 inhibitor on radiation-induced c-jun activation in DT40cells.

B-cell signal transduction events direct fundamental decisions regarding cell survival during periods of oxidative stress. A better understanding of the dynamic interplay between B-cell signaling pathways is needed to determine how vital decisions are dictated during intracellular oxidation changes. STAT proteins (signal transducers and activators of transcription) are a family of DNA binding proteins that were identified during a search for interferon (IFN) a- or g-stimulated gene transcription targets. There are presently seven STAT family members. The JAK family of cytoplasmic protein kinases were originally demonstrated to also function in IFN signaling, and are now known to participate in a broad range of receptor-activated signal cascades. Different ligands and cell activators employ specific JAK and STAT family members. The basic model for STAT activation suggests that in unstimulated cells, latent forms of STATs are predominantly localized within the cytoplasm. Ligand binding induces STAT proteins to associate with intracellular phosphotyrosine residues of transmembrane receptors. Once STATs are bound to receptors, receptor-associated JAK kinases phosphorylate the STAT proteins. STAT proteins then dimerize through specific reciprocal SH2-phosphotyrosine interactions and may form complexes with other DNA-binding proteins. STAT complexes translocate to the nucleus and interact with DNA response elements to enhance transcription of target genes. Signaling events regulating apoptotic responses have been shown to utilize STAT proteins. Notably, a recent study demonstrated JAK activation by tyrosine phosphorylation in cells that are exposed to reactive oxygen intermediates, which in-turn lead to tyrosine phosphorylation and activation of STAT-1, STAT-3 and STAT-6.

After establishing that LYN, BTK, and SYK kinases are not required for radiation-induced c-jun activation, we set out to determine if c-jun activation is functionally linked to the JAK-STAT pathway. To this end, we examined the effects of a JAK-3 inhibitory novel quinazoline derivative on c-jun expression levels in irradiated DT-40 cells. To identify a potent JAK-3 specific inhibitor, the effects of two novel quinazoline derivatives on the enzymatic activity of JAK-1, JAK-2, and JAK-3 were examined using Sf21 cells that were infected with baculovirus expression vectors for these kinases, using standard methods (FIG. 4). Infected cells were harvested, JAKs were immunoprecipitated with appropriate antibodies (anti-JAK-1: (HR-785), cat# sc-277, rabbit polyclonal IgG affinity purified, 0.1 mg/ml, Santa Cruz Biotechnology; anti-JAK-2: (C-20)-G, cat # sc-294-G, goat polyclonal IgG affinity purified, 0.2 mg/ml, Santa Cruz Biotechnology; anti-JAK-3: (C-21), cat # sc-513, rabbit polyclonal IgG affinity purified, 0.2 mg/ml, Santa Cruz Biotechnology), and kinase assays were performed following a 1 hour exposure of the immunoprecipitated Jaks to the quinazoline compounds, as described by Uckun, F. M., Waddick, K. G., Mahajan, S., Jun, X., Takata, M., Bolen, J., and Kurosaki, T. *Science.* 273: 1096–100, 1996; Uckun F. M., Evans W. E., Forsyth C. J., Waddick K. G., T-Ahlgren L., Cheistrom L. M., Burkhardt A., Bolen J., Myers D.E. *Science* 267:886–891, 1995; and Myers D. E., Jun X., Waddick K. G., Forsyth C., Cheistrom L. M., Gunther R. L., Turner N. E., Bolen J., Uckun F. M. *Proc Nat'l Acad Sci USA* 92: 9575–9579, 1995; and Tuel Ahlgren, L., Jun, X., Waddick, K. G., Jin, J., Bolen, J., and Uckun, F. M. *Leuk Lymphoma.* 20: 417–26, 1996.

Figure 4C:
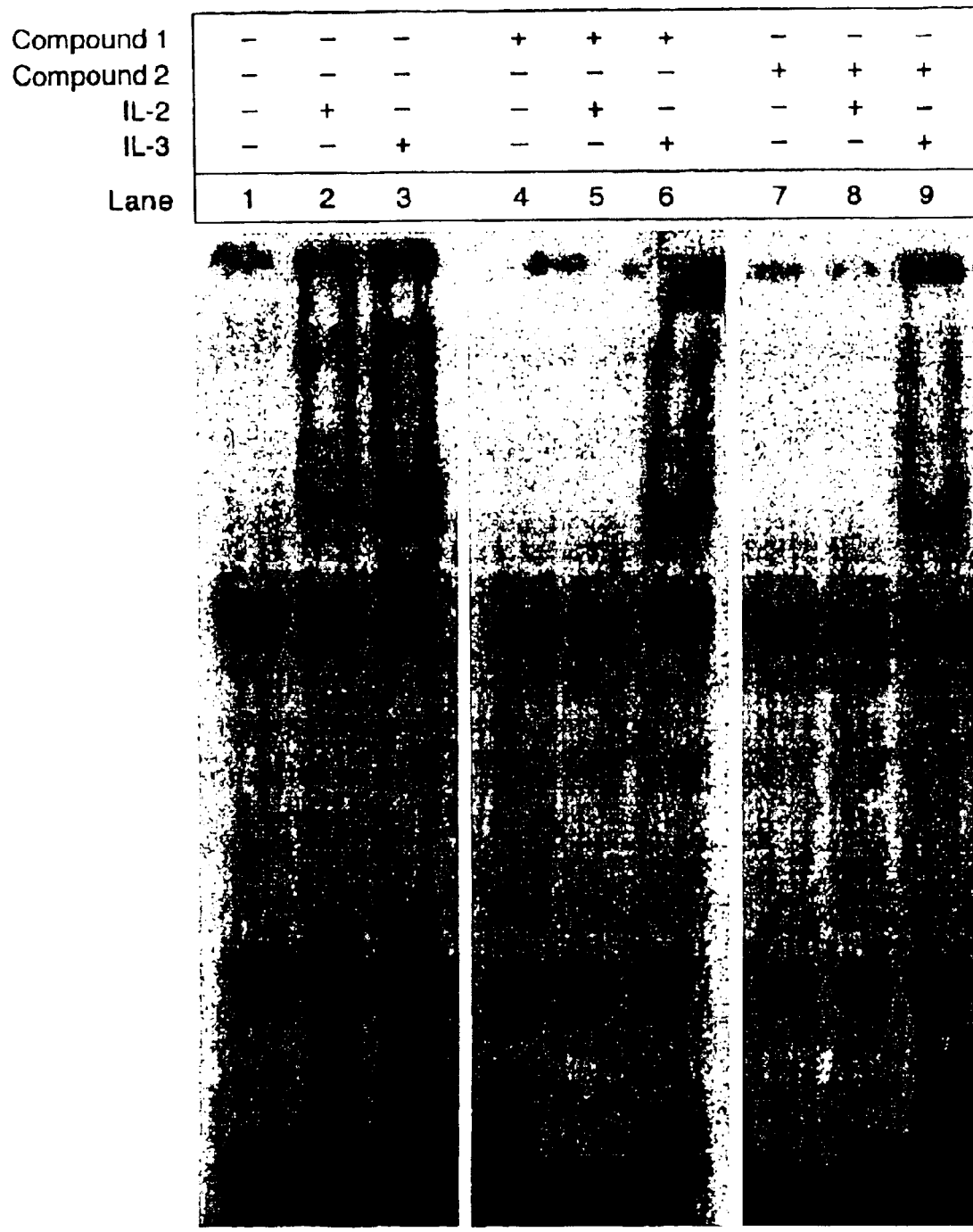

As shown in FIG. 4B, both compounds inhibited JAK-3 (FIGS. B.3 and B.4) but not JAK-1 (FIG. B.1) or JAK-2 (FIG. B.2) (FIG. 4D). Electrophoretic Mobility Shift Assays (EMSAs) were performed to examine the effects of both compounds on cytokine-induced STAT activation. Specifically, 32Dc11/IL2Rβ cells (gift from James Ihle, St. Jude Children's Research Hospital) were exposed at 8×10⁶/ml in RPMI supplemented with FBS to the JAK-3 inhibitors at a final concentration of 10 μg/ml in 1% DMSO) for 1 hour and subsequently stimulated with IL2 or IL3 as indicated. Cells were collected after 15 minutes and resuspended in lysis buffer (100 mM Tris-HCl pH 8.0, 0.5% NP-40, 10% glycerol, 100 mM EDTA, 0.1 mM NaVO3, 50 mM NaF, 150 mM Nacl, 1 mM DTT, 3 (g/ml Aprotinin, 2 g/ml Pepstatin A, 1 (g/ml Leupeptin and 0.2 mM PMSF). Lysates were precleared by centrifugation for 30 minutes. Cell extracts (approximately 10 g) were incubated with 2 μg of poly(dI-dC) for 30 minutes, followed by a 30 minute incubation with 1 ng of poly nucleotide kinase-$^{32}$P labeled double stranded DNA oligonucleotide representing the IRF-1 STAT DNA binding sequence (Santa Cruz Biotechnology, Santa Cruz, Calif.). Samples were resolved by nondenaturing PAGE and visualized by autoradiography. As shown in FIG. 4C, both compounds inhibited the JAK-3-dependent STAT activation after stimulation with IL-2, but they did not affect the JAK-1/JAK-2-dependent STAT activation after stimulation with IL3. Compound 2 was selected for further experiments designed to examine the effects of JAK-3 inhibition on radiation-induced c-jun activation.

As shown in FIG. 5, ionizing radiation failed to induce c-jun expression in DT-40 cells treated with the JAK-3 inhibitor. This demonstrates that JAK-3 inhibitors are capable of inhibiting radiation induced c-jun expression.

In untreated cells, c-jun expression is induced by exposure to DNA-damaging chemical agents and by exposure to radiation. Thus, c-jun expression is an early marker of cellular response to such DNA-damaging agents. It has been shown that compounds that inhibit JAK-3 are capable of inhibiting the expression of c-jun. Accordingly, JAK-3 inhibitors may be useful to prevent or treat diseases or conditions that result from exposure to DNA-damaging agents.

JAK-3 maps to human chromosome 19p12–13.1. A cluster of genes encoding protooncogenes and transcription factors is also located near this region. JAK-3 expression has been demonstrated in mature B-cells as well as B-cell precursors. JAK-3 has also been detected in leukemic B-cell precursors and lymphoma B-cells. The physiological roles for JAK-3 have been borne out through targeted gene disruption studies in mice, the genetic analysis of patients with severe combined immunodeficiency, and biochemical studies of JAK-3 in cell lines. A wide range of stimuli result in JAK-3 activation in B-cells, including interleukin 7 and interleukin 4. The B-cell marker CD40 constitutively associates with JAK-3 and ligation of CD40 results in JAK-3 activation which has been shown to be mandatory for CD40-mediated gene expression. Constitutive activity of JAK-3 has been observed in v-abl transformed pre-B cells and coimmunoprecipitations show that v-abl physically associates with JAK-3 implicating JAK-3 in v-abl induced cellular transformation. See Ihle, J. N. "Janus kinases in cytokine signalling," *Philos Trans R Soc Lond B Biol Sci* 351:159–66, 1996; Leonard, W. J. "STATs and cytokine specificity," *Nat Med* 2:968–9, 1996; Levy, D. E. "The house that Jak/Stat built," *Cytokine Growth Factor Rev* 8:81–90, 1997; Riedy, M. C. et al. "Genomic sequence, organization, and chromosomal localization of human JAK-3," *Genomics* 37, 57–61, 1996; Safford, M. G., Levenstein, M., Tsifrina, E., Amin, S., Hawkins, A. L., Griffin, C. A., Civin, C. I. and Small, D. "JAK-3: expression and mapping to chromosome 19p12–13.1" [published erratum appears in *Exp Hematol* 1997 Jul;25(7):650]. *Exp Hematol* 25, 374–86, 1997; Kumar, A., Toscani, A., Rane, S. and Reddy, E. P. "Structural organization and chromosomal mapping of JAK-3 locus," *Oncogene* 13, 2009–14, 1996; Hoffman, S. M., Lai, K. S., Tomfohrde, J., Bowcock, A., Gordon, L. A. and Mohrenweiser, H. W. "JAK-3 maps to human chromosome 19p12 within a cluster of proto-oncogenes and transcription factors," *Genomics* 43, 109–111, 1997; Tortolani, P. J. et al. "Regulation of JAK-3 expression and activation in human B cells and B cell malignancies," *J Immunol* 155, 5220–6, 1995; Sharfe, N., Dadi, H. K., J J, O.S. and Roifman, C. M. "JAK-3 activation in human lymphocyte precursor cells," *Clin Exp Immunol* 108, 552–6, 1997; Gurniak, C. B. and Berg, L. J. "Murine JAK-3 is preferentially expressed in hematopoietic tissues and lymphocyte precursor cells," *Blood* 87, 3151–60, 1996; Rolling, C., Treton, D., Beckmann, P., Galanaud, P. and Richard, Y. "JAK-3 associates with the human interleukin 4 receptor and is tyrosine phosphorylated following receptor triggering," *Oncogene* 10, 1757–61, 1995; Rolling, C., Treton, D., Pellegrini, S., Galanaud, P. and Richard, Y. "IL4 and IL13 receptors share the gamma c chain and activate STAT6, STAT3 and STAT5 proteins in normal human B cells," *FEBS Lett* 393, 53–6, 1996; Hanissian, S. H. and Geha, R. S. "JAK-3 is associated with CD40 and is critical for CD40 induction of gene expression in B cells," *Immunity* 6, 379–87, 1997; Danial, N. N., Pernis, A. and Rothman, P. B. "Jak-STAT signaling induced by the v-abl oncogene," *Science* 269, 1875–7, 1995.

SUMMARY

Exposure of B-lineage lymphoid cells to ionizing radiation induces an elevation of c-jun protooncogene mRNA levels. This signal is abrogated by protein tyrosine kinase (PTK) inhibitors, indicating that activation of an as yet unidentified PTK is mandatory for radiation-induced c-jun expression. Experimental evidence shows that the cytoplasmic tyrosine kinases BTK, SYK and LYN are not required for this signal. Lymphoma B-cells rendered deficient for LYN, SYK or both by targeted gene disruption showed increased c-jun expression levels after radiation exposure, but the magnitude of the stimulation was lower than in wild-type cells. Thus, these PTK may participate in the generation of an optimal signal. Notably, inhibitors of Janus family kinase 3 (JAK-3) abrogated radiation-induced c-jun activation. This suggests that JAKs are important regulators of radiation-induced c-jun activation, and that JAK-3 inhibitors are useful for preventing or treating diseases or conditions that result from chemical-induced or radiation-induced c-jun activation.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A method for specifically inhibiting c-jun activation in mammalian or avian cells comprising contacting the cells with an effective inhibitory amount of a compound of formula I:

wherein

X is HN, $R_{11}$N, S, O, $CH_2$, or $R_{11}$CH;

$R_{11}$, is hydrogen ($C_1$–$C_4$)alkyl, or ($C_1$–$C_4$)alkanoyl;

$R_1$–$R_8$ are each independently hydrogen, hydroxy, mercapto, amino, nitro, ($C_1$–$C_4$)alkyl, ($C_1$–$C_4$)alkoxy, ($C_1$–$C_4$)alkylthio, or halo; wherein two adjacent groups of $R_1$–$R_5$ together with the phenyl ring to which they are attached may optionally form a fused ring; and further wherein the ring formed by the two adjacent groups of $R_1$–$R_5$ may optionally be substituted by 1, 2, 3, or 4 hydroxy, mercapto, amino, nitro, ($C_1$–$C_4$)alkyl, ($C_1$–$C_4$)alkoxy, ($C_1$–$C_4$)alkylthio, or halo; and $R_9$ and $R_{10}$ are each independently hydrogen, ($C_1$–$C_4$) alkyl, ($C_1$–$C_4$)alkoxy, halo, or ($C_1$–$C_4$)alkanoyl; or $R_9$ and $R_{10}$ together are methylenedioxy, or a pharmaceutically acceptable salt thereof.

2. The method of claim 1 wherein the compound is 4-(3'-bromo-4'-hydroxylphenyl)-amino-6,7-dimethoxyquinazoline or a pharmaceutically acceptable salt thereof.

3. The method of claim 1 wherein the compound is 4-(4'-hydroxylphenyl)-amino-6,7-dimethoxyquinazoline or a pharmaceutically acceptable salt thereof.

4. The method of claim 1 wherein the contacting is performed in vitro.

5. The method of claim 1 wherein the contacting is performed in vivo.

6. The method of claim 1 wherein the cells are mammalian.

7. The method of claim 1 wherein the cells are human.

8. The method of claim 1 wherein the cells are avian.

* * * * *

SEQUENCE LISTING

```
<160> NUMBER OF SEQ ID NOS: 6

<210> SEQ ID NO 1
<211> LENGTH: 22
<212> TYPE: DNA
<213> ORGANISM: Gallus gallus

<400> SEQUENCE: 1
actctgcacc caactacaac gc                                          22

<210> SEQ ID NO 2
<211> LENGTH: 22
<212> TYPE: DNA
<213> ORGANISM: Gallus gallus

<400> SEQUENCE: 2
cttctaccgt cagctttacg cg                                          22

<210> SEQ ID NO 3
<211> LENGTH: 24
<212> TYPE: DNA
<213> ORGANISM: Gallus gallus

<400> SEQUENCE: 3
agaggtgctg cccagaacat catc                                        24

<210> SEQ ID NO 4
<211> LENGTH: 23
<212> TYPE: DNA
<213> ORGANISM: Gallus gallus

<400> SEQUENCE: 4
gtggggagac agaagggaac aga                                         23
```

```
<210> SEQ ID NO 5
<211> LENGTH: 22
<212> TYPE: DNA
<213> ORGANISM: Gallus gallus

<400> SEQUENCE: 5
gccctcttcc agcatctttc tt                                        22

<210> SEQ ID NO 6
<211> LENGTH: 20
<212> TYPE: DNA
<213> ORGANISM: Gallus gallus

<400> SEQUENCE: 6
tttatgcgca tttatgggtt                                           20
```